(12) United States Patent
Huang et al.

(10) Patent No.: US 12,422,364 B2
(45) Date of Patent: Sep. 23, 2025

(54) FLUORESCENCE SPECTRAL SHAPE ANALYSIS FOR ANALYTE RECOGNITION

(71) Applicant: THE BOARD OF REGENTS OF THE UNIVERSITY OF TEXAS SYSTEM, Austin, TX (US)

(72) Inventors: Yun Huang, San Antonio, TX (US); Zhiliang Li, San Antonio, TX (US); Kirk Schanze, Helotes, TX (US); April Risinger, San Antonio, TX (US)

(73) Assignee: Board of Regents, The University of Texas System, Austin, TX (US)

( * ) Notice: Subject to any disclaimer, the term of this patent is extended or adjusted under 35 U.S.C. 154(b) by 814 days.

(21) Appl. No.: 16/976,546

(22) PCT Filed: Feb. 28, 2019

(86) PCT No.: PCT/US2019/020109
§ 371 (c)(1),
(2) Date: Aug. 28, 2020

(87) PCT Pub. No.: WO2019/169169
PCT Pub. Date: Sep. 6, 2019

(65) Prior Publication Data
US 2021/0003506 A1 Jan. 7, 2021

Related U.S. Application Data

(60) Provisional application No. 62/672,899, filed on May 17, 2018, provisional application No. 62/636,823, filed on Feb. 28, 2018.

(51) Int. Cl.
*G01N 21/64* (2006.01)
*G01N 33/533* (2006.01)
*G01N 33/542* (2006.01)

(52) U.S. Cl.
CPC ....... *G01N 21/6428* (2013.01); *G01N 33/533* (2013.01); *G01N 33/542* (2013.01); *G01N 2458/10* (2013.01)

(58) Field of Classification Search
CPC . G01N 21/6428; G01N 33/533; G01N 33/542
See application file for complete search history.

(56) References Cited

U.S. PATENT DOCUMENTS 6,201,989 B1 3/2001 Whitehead et al.
6,627,748 B1 9/2003 Ju et al.
(Continued)

FOREIGN PATENT DOCUMENTS

WO WO 2014/127379 8/2014

OTHER PUBLICATIONS

A conjugated polyelectrolyte with pendant high dense short alkyl chain bridged cationic ions: analyte induced light up and label free fluorescent sensing of tumor markers. Nina Fu, Yijiao Wang, Dan Liu, Caixia Zhang, Shao Su, Biqing Bao, Baomin Zhao, Lianhui Wang Polymers 2017, 9, 227 (Year: 2017).*

(Continued)

*Primary Examiner* — Lyle Alexander
*Assistant Examiner* — Dwan A Gerido

(57) ABSTRACT

The inventors describe the use of a polymeric marker, in certain aspects the polymeric marker is conjugated polymeric marker such as P-C-3. Other aspects are directed to methods of analyzing the conjugated marker fluorescence spectral shape, which is strongly dependent on the local/ionic environment. This fluorescence marker is able to interact with and classify various analytes.

5 Claims, 10 Drawing Sheets

Specification includes a Sequence Listing.

(56) References Cited

U.S. PATENT DOCUMENTS

2002/0150759 A1    10/2002    Jones et al.
2009/0221099 A1*    9/2009    Rotello ................ G01N 33/542
                                                                                                                 436/501
2015/0005188 A1    1/2015    Levner et al.

OTHER PUBLICATIONS

Two photon absorption of cationic conjugated polyelectrolytes: effects of aggregation and application of 2-photon-sensitized fluorescence from green fluorescent protein Wang et al. Chem. Mater. 2017, 29,3295-3303 (Year: 2017).*

International Search Report and Opinion issued in PCT Application No. PCT/US2019/020109 mailed on May 28, 2019.

Li et al., "Photophysics and phosphate fluorescence sensing by poly(phenylene ethynylene) conjugated polyelectrolytes with branched ammonium side groups" *Journal of Materials Chemistry C* Jun. 2018, 3722-3730.

Wang et al., "Two-Photon Absorption of Cationic Conjugated Polyelectrolytes: Effects of Aggregation and Application to 2-Photon-Sensitized Fluorescence from Green Fluorescent Protein" *Chem. Mater.* 2017, 29(7), 3295-3303.

Yang et al., "Pyrophosphate Sensor Based on Principal-Component Analysis of Conjugated Polyelectrolyte Fluorescence" *ACS Omega* 2016, 1(4), 648-655.

\* cited by examiner

SEQUENCE LISTING

<160> NUMBER OF SEQ ID NOS: 4

<210> SEQ ID NO 1
<211> LENGTH: 21
<212> TYPE: DNA
<213> ORGANISM: Artificial Sequence
<220> FEATURE:
<223> OTHER INFORMATION: synthetic oligonucletoide

<400> SEQUENCE: 1
ctgtggattg gagcgattct t                                              21

<210> SEQ ID NO 2
<211> LENGTH: 21
<212> TYPE: DNA
<213> ORGANISM: Artificial Sequence
<220> FEATURE:
<223> OTHER INFORMATION: synthetic oligonucleotide

<400> SEQUENCE: 2
ttacaacggc tgatagcacc a                                              21

<210> SEQ ID NO 3
<211> LENGTH: 34
<212> TYPE: DNA
<213> ORGANISM: Artificial Sequence
<220> FEATURE:
<223> OTHER INFORMATION: synthetic oligonucleotide

<400> SEQUENCE: 3
gtaggttggt gtggtcgcct tcagagtgcg gaag                                34

<210> SEQ ID NO 4
<211> LENGTH: 34
<212> TYPE: DNA
<213> ORGANISM: Artificial Sequence
<220> FEATURE:
<223> OTHER INFORMATION: synthetic oligonucleotide

<400> SEQUENCE: 4
cttccgcact ctgaaggcga ccacaccaac ctac                                34

FLUORESCENCE SPECTRAL SHAPE ANALYSIS FOR ANALYTE RECOGNITION

CROSS REFERENCE TO RELATED APPLICATIONS

This Application is a national phase application under 35 U.S.C. § 371 of International Application No. PCT/US2019/020109, filed Feb. 28, 2019, which claims priority to U.S. Provisional Patent application Ser. No. 62/636,823 filed Feb. 28, 2018 and 62/672,899 filed May 17, 2018, both of which are incorporated herein by reference in their entirety.

STATEMENT REGARDING FEDERALLY FUNDED RESEARCH

This invention was made with government support under Grant No. CHE-1737714, awarded by the National Science Foundation. The government has certain rights to the invention.

BACKGROUND OF THE INVENTION

The invention generally concerns methods and compositions for fluorescent detection. In particular, aspect are directed to embodiments for detecting molecules using polycationic polymers.

Fluorescence markers or probes have widespread application in high-throughput and high-content screening technologies which are widely used in cancer research for identifying potential drug candidates and disease detection. However, most markers are specifically designed to recognize a single target, so selection of markers requires prior-knowledge about the target and identification results are affected by prior knowledge. As a trade-off between accuracy and computational complexity, for most current markers, only one variable such as the intensity of a single wavelength or the average of certain wavelengths from the emission spectrum is collected and analyzed, and the information contained in the emission shape cannot be utilized.

SUMMARY OF THE INVENTION

Embodiments include the use of a polymeric marker, in certain aspects the polymeric marker is a conjugated polymeric marker (e.g., conjugated polyelectrolyte (CPE)), such as P-C-3. Certain aspects are directed to methods of analyzing the conjugated marker's fluorescence spectral shape, which is strongly dependent on the local/ionic environment. This fluorescence marker is able to interact with and classify various analytes. In particular aspects the fluorescent marker or polycationic polymer can identify at least 12 kinds of nucleoside phosphates (NTP, NDP, and NMP; N=A, C, G, and U) in a short time, e.g., 1 minute or less and can achieve 100% classification accuracy. Binding or interaction with other molecules or targets can also be determined, e.g., polynucleotides and analogs thereof. By mixing a conjugated marker, e.g. (P-C-3)n, solution with different nucleoside phosphates (e.g., P-C-3 mixed with one nucleoside phosphate in each well of a 96-well plate), the fluorescence spectrum of each mixed solution is collected (e.g., by the plate reader). By analyzing the fluorescence spectral shapes, the inventors demonstrate that fluorescence spectral shapes of the polymer are sensitive to both the charge and the structure of analytes.

In certain aspects, the analyte is a peptide, polypeptide, carbohydrate, lipid, or combination thereof. In other aspects, the polypeptide can be a cell surface receptor, enzyme, or antibody. The analyte can also be a one or more of a nucleoside, nucleotide, nucleotide diphosphate, nucleotide triphosphate, or a nucleotide polymer or analog thereof. The nucleotide polymer (polynucelotide, e.g., DNA or RNA) or analog thereof can be 2, 5, 10, 15, 20, 25, 30, 35, 40, 45, 50, 75, 100, 200, 400, 800, 1600, 3200 to 5000 nucleotides or nucleotide analogs, including all values and ranges there between. In particular aspects, the analyte is a nucleoside phosphate.

Other embodiments are directed to methods and algorithm to select useful features from the fluorescence spectrum to reduce computational complexity and prevent overfitting. In particular methods three wavelengths are selected from the entire spectrum by a wrapped feature selection algorithm. By just measuring the normalized intensity of these 3 selected wavelengths, the inventors are able to achieve up to 100% classification accuracy for at least 12 kinds of nucleoside phosphates (test set: 12 nucleoside phosphates X 3 replicates) in 3 minutes by linear discriminant analysis (LDA). This is the first classification method to utilize the information contained in fluorescence spectrum shapes of a polymeric marker. With the feature selection algorithm, measuring the normalized intensity of a few selected wavelengths instead of the whole fluorescence spectrum drastically reduces the measurement time, which reveals the potential of fluorescence spectrum shape analysis in high-throughput screening. By analyzing high-dimensional spectral data, developing a universal marker for high-accuracy classification and clustering of cell type and phenotype becomes possible, which is also under investigation.

Examples of a fluorescent polymer or polycationic polymer is P-C-3 or P-O-3, the structure of which if provided below.

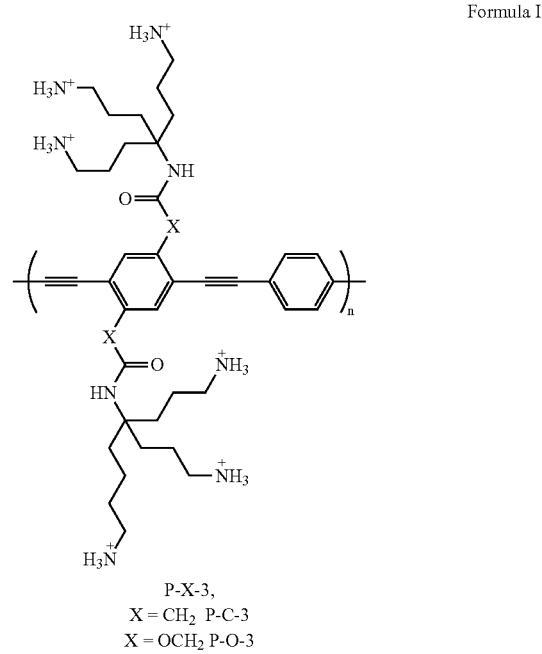

Formula I

P-X-3,
X = CH$_2$ P-C-3
X = OCH$_2$ P-O-3

-continued

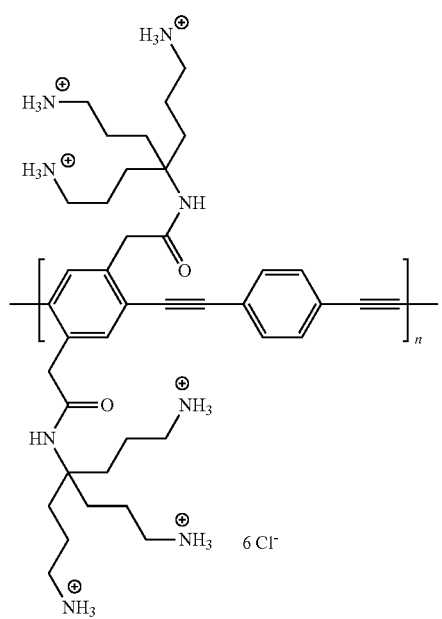

Formula II

P-C-3

In certain aspects x is C1 to C3 alkyl or alkoxy group, and n can be 3, 4, 5, 6, 7, 8, 9, 10 11, 12, 13, 14, 15, 16,17, 18, 19, 20, 100, 200, 300, 400, 500, 600, 700, 800, 900, 1000 or more, including all values and ranges there between.

As used herein the term "analyte" refers to a compound or composition to be detected or measured and which binds or interacts with polymeric marker. The analyte can be any substance that binds, interacts, aggregates, or associates directly or indirectly with a polymeric marker, for example a carbohydrate, lectin, hormone, receptor, nucleic acids, and the like. Possible analytes include virtually any compound, composition, aggregation, or other substance which may be detected using the compositions and methods described herein.

Analytes include, but are not limited to, toxins, organic compounds, proteins, peptides, microorganisms, bacteria, viruses, amino acids, nucleic acids, carbohydrates, hormones, steroids, vitamins, drugs (including those administered for therapeutic purposes as well as those administered for illicit purposes), pollutants, pesticides, and metabolites of or antibodies to any of the above substances. The term analyte also includes any antigenic substances, haptens, antibodies, macromolecules, and combinations thereof. A non-exhaustive list of exemplary analytes is set forth in U.S. Pat. No. 4,366,241, the disclosure of which is incorporated herein by reference. Further descriptions and listings of representative analytes are found in U.S. Pat. Nos. 4,299, 916; 4,275,149; and 4,806,311, all incorporated herein by reference.

Other embodiments of the invention are discussed throughout this application. Any embodiment discussed with respect to one aspect of the invention applies to other aspects of the invention as well and vice versa. Each embodiment described herein is understood to be embodiments of the invention that are applicable to all aspects of the invention.

It is contemplated that any embodiment discussed herein can be implemented with respect to any method or composition of the invention, and vice versa.

The use of the word "a" or "an" when used in conjunction with the term "comprising" in the claims and/or the specification may mean "one," but it is also consistent with the meaning of "one or more," "at least one," and "one or more than one."

The term "about" or "approximately" are defined as being close to as understood by one of ordinary skill in the art. In one non-limiting embodiment the terms are defined to be within 10%, preferably within 5%, more preferably within 1%, and most preferably within 0.5%.

The term "substantially" and its variations are defined to include ranges within 10%, within 5%, within 1%, or within 0.5%.

The terms "inhibiting" or "reducing" or "preventing" or any variation of these terms includes any measurable decrease or complete inhibition to achieve a desired result.

The term "effective," as that term is used in the specification and/or claims, means adequate to accomplish a desired, expected, or intended result.

The terms "wt. %," "vol. %," or "mol. %" refers to a weight, volume, or molar percentage of a component, respectively, based on the total weight, the total volume, or the total moles of material that includes the component. In a non-limiting example, 10 moles of component in 100 moles of the material is 10 mol. % of component.

The use of the term "or" in the claims is used to mean "and/or" unless explicitly indicated to refer to alternatives only or the alternatives are mutually exclusive, although the disclosure supports a definition that refers to only alternatives and "and/or."

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

The compositions and methods of making and using the same of the present invention can "comprise," "consist essentially of," or "consist of" particular ingredients, components, blends, method steps, etc., disclosed throughout the specification.

Other objects, features and advantages of the present invention will become apparent from the following detailed description. It should be understood, however, that the detailed description and the specific examples, while indicating specific embodiments of the invention, are given by way of illustration only, since various changes and modifications within the spirit and scope of the invention will become apparent to those skilled in the art from this detailed description.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of the specification embodiments presented herein.

DETAILED DESCRIPTION OF THE INVENTION

Figure 1:
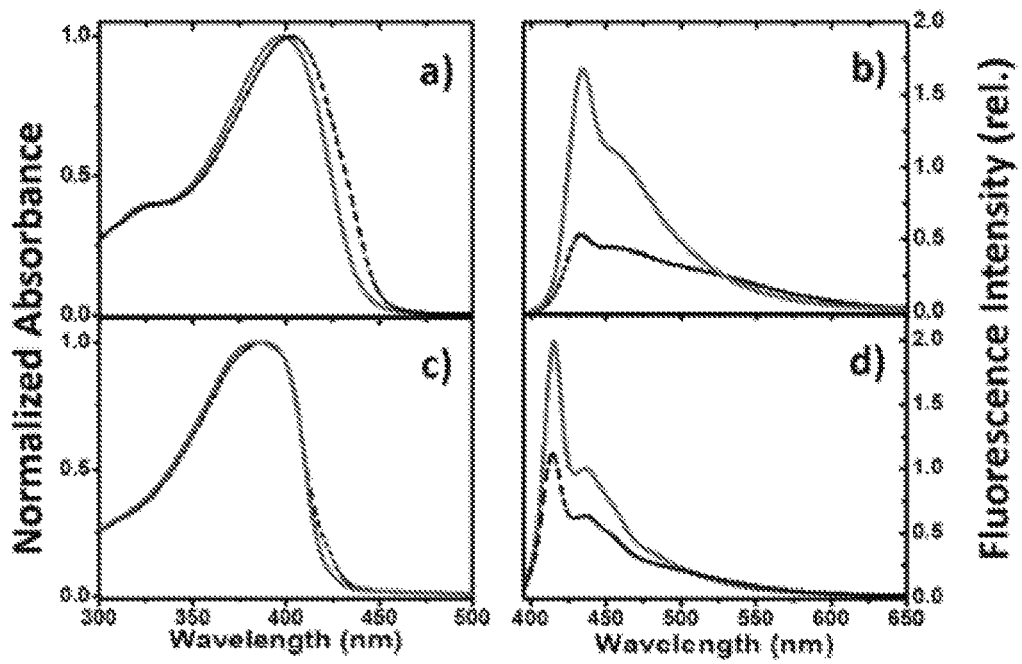
FIG. 1A-1D Normalized absorption (a) and relative fluorescence (b) of P-O-3 in methanol and in water (dotted lines). Normalized absorption (c) and fluorescence (d) of P-C-3 in methanol and in water (dotted black lines).
Figure 2:
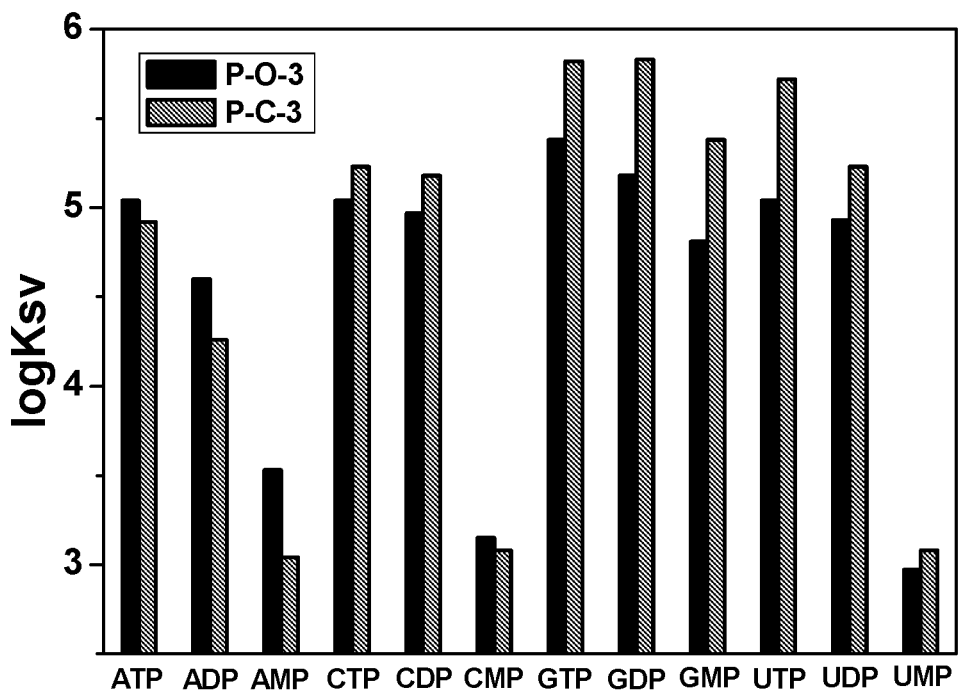
FIG. 2. LogKsv values for nucleoside phosphates in Fluorescence Quenching of P-O-3 (left columns) and P-C-3 (right columns) in 10 µM polymer solution in MES buffer at pH 6.5.

Fluorescence markers have found widespread application in high-throughput and high-content screening technologies, which are widely used in cancer research for identifying potential drug candidates and disease detection. However, most markers are specifically designed to recognize a single target, so selection of markers requires pre-knowledge about the target and identification of results are affected by prior knowledge. As a trade-off between accuracy and computational complexity, for most current markers, only one variable such as the intensity of a single wavelength or the average of certain wavelengths from the emission spectrum is collected and analyzed, and the information contained in the emission shape can't be utilized.

Fluorescent emission line shape of a CPE is sensitive to primary structures. The emission shape analysis can be used to provide data and analysis that is robust in regard to random experimental variations. After feature selection, methods are capable of classify at least 13 different nucleoside phosphates in 1 minute and achieves 100% classification accuracy without overfitting. Single-molecule spectroscopy reveals that the shape of the emission spectra results from a distribution of chromophores with a variety of conjugation lengths. The fluorescence properties most often characterize those of the few low transition-energy exciton traps in a conjugated polymer molecule.

A. POLYMERIC MARKERS/PROBES

Various samples can be probed or contacted with a polymeric marker (polycationic polymer) where the polymeric marker interacts with components of the sample and provides an environment specific signal. In certain aspects, the polymeric marker is a conjugated polymeric marker (e.g., conjugated polyelectrolyte (CPE)), an example of which is described below. In certain aspects the polymeric marker is a conjugated polymeric marker or conjugated polyelectrolyte (CPE), such as (P-C-3)n. Certain aspects are directed to methods of analyzing the conjugated marker's fluorescence spectral shape, which is strongly dependent on the local/ionic environment, and using this response to characterize a sample. The sample can contain 1, 2, 3, 4, 5, 6, 7 8, 9, 10 or more components that bind or interact, dependently or independently, with the polymeric marker. These polymeric markers and be used as probes to characterize a sample or analytes in a sample. The sample can be a biological or environmental sample. In certain instance the sample is or is developed or diluted into a liquid sample, e.g., an aqueous sample.

Polymeric markers are represented by the compounds of Formula I and/or Formula II.

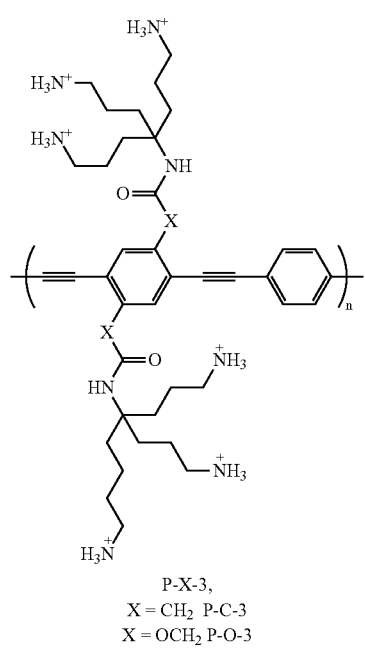

P-X-3,
X = CH$_2$ P-C-3
X = OCH$_2$ P-O-3

Formula I

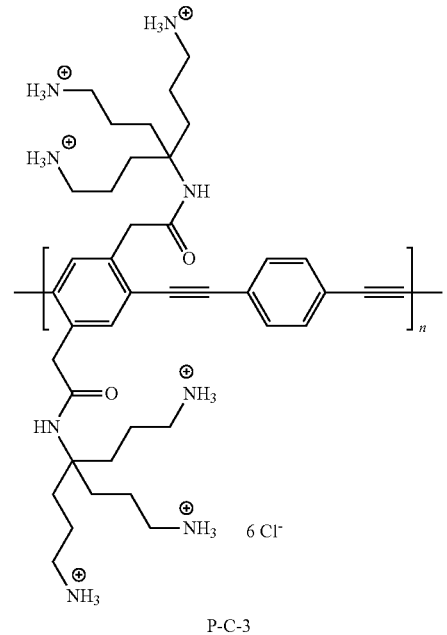

P-C-3

Formula II

In certain aspects x is C1 to C3 alkyl or alkoxy group, and n can be 3, 4, 5, 6, 7, 8, 9, 10 11, 12, 13, 14, 15, 16,17, 18, 19, 20 to 100 or more. One can optimize the assay given a different polymer and/or a polymer of varying lengths.

Synthesis of M-O-3. The compound was synthesized following the method described in Zhao and Schanze, *Chem. Commun.*, 2010, 46, 6075-6077, but using compound 6 as the amine. $^1$H NMR (CDCl$_3$, 300 MHz, δ ppm): 7.14 (s, 2H), 6.55 (br, s, 2H), 4.66 (br, s, 6H), 4.34 (s, 4H), 3.03 (m, 12H), 1.76 (m, 12H), 1.45 (m; 12H), 1.43 (s, 54H). $^{13}$C NMR (CDCl$_3$, 75 MHz, δ ppm): 166.0, 156.2, 151.7 122.7, 86.5, 79.4, 68.7, 58.9, 40.9, 32.9, 28.7, 24.2. HRMS: (ESI+) m/z calcd for C$_{60}$H$_{104}$I$_2$N$_8$O$_{16}$[(M+H)]$^+$ 1447.5732, found 1447.5706.

Scheme for synthesis of compound 6

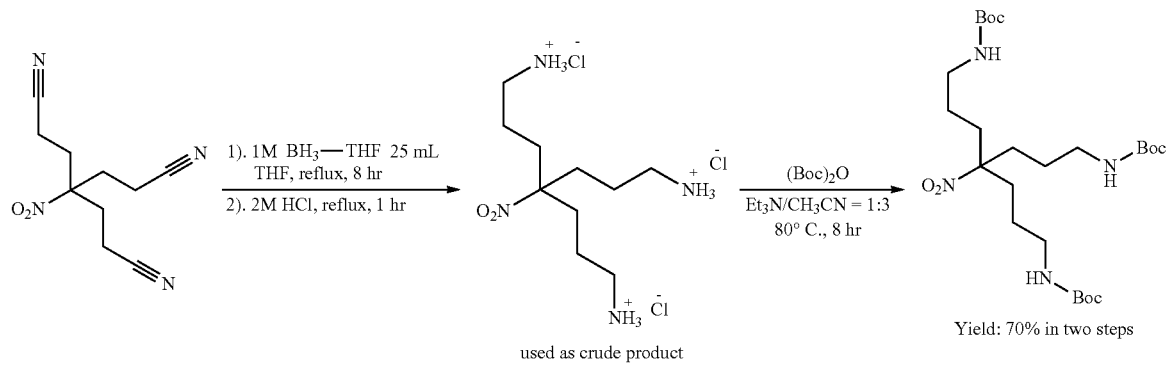

-continued
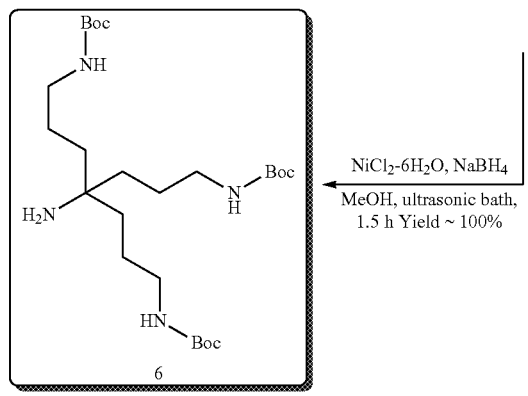
Scheme for synthesis of M-O-3
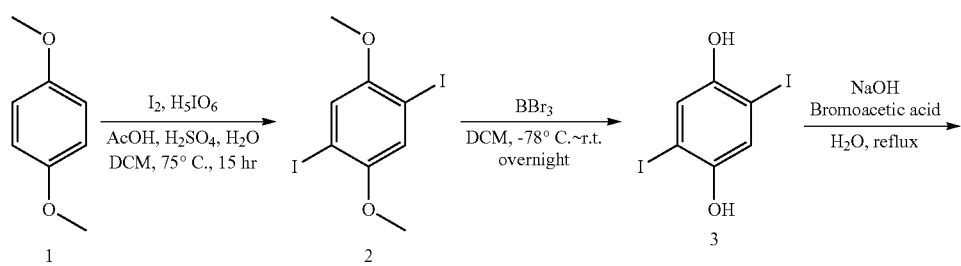
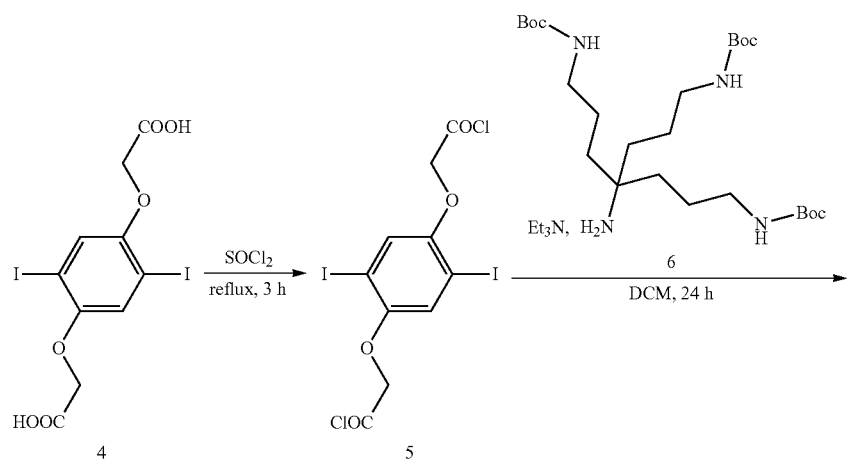

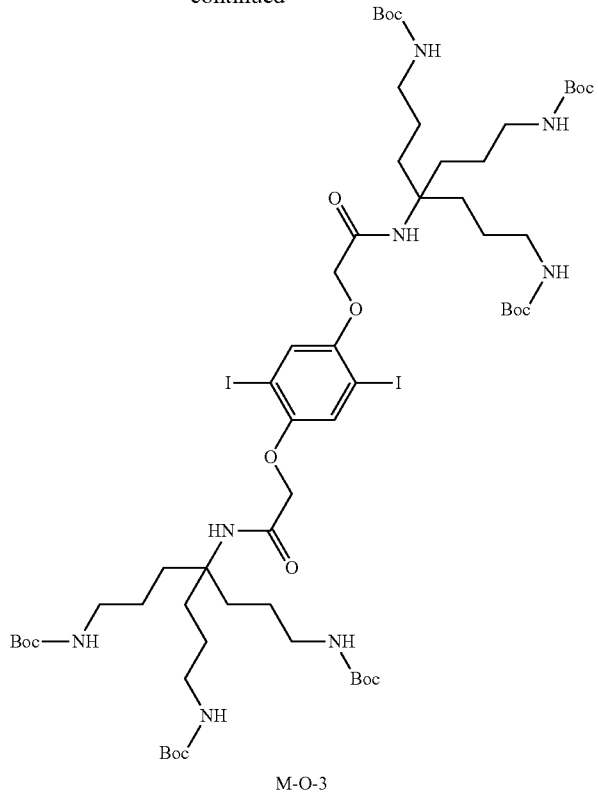 [SMILES: CC(C)(C)OC(=O)NCCCC(CCCNC(=O)OC(C)(C)C)(CCCNC(=O)OC(C)(C)C)NC(=O)COc1cc(I)c(OCC(=O)NC(CCCNC(=O)OC(C)(C)C)(CCCNC(=O)OC(C)(C)C)CCCNC(=O)OC(C)(C)C)cc1I]

M-O-3

Synthesis of 2,20-(2,5-diiodo-1,4-phenylene)diacetic acid (8) Compound 8 was synthesized according to a modified literature procedure.(Kraszkiewicz et al., *Synthesis*, 2006, 1195-1199) Iodine (1.2 g, 4.73 mmol) and $KIO_4$ (0.34 g, 1.59 mmol) were slowly added to 95% $H_2SO_4$ (30 mL). After stirring for 3 h at 25-30° C., a dark brown iodinating solution containing $I^+$ intermediate (2.2 equiv.) was obtained. 1,4-Phenylenediacetic acid (0.95 g, 5 mmol) was added in one portion to the brown iodinating solution and the resulting solution was stirred at 25-30° C. for 3 h. The light brown solution was cooled down to room temperature and poured on ice. The precipitate was collected by filtration, thoroughly washed with ice cold saturated aqueous $Na_2S_2O_3$ solution and water until the filtrates were neutral and followed by washing with ethanol. The raw product was recrystallized from ethanol (50 mL) to afford the product as a white solid (1.622 g, 3.64 mmol, 70%). $^1H$ NMR (300 MHz, DMSO-d6): δ 3.68 (s, 4H), 7.82 (s, 2H), 12.53 (s; 2H). $^{13}C$ NMR (75 MHz, DMSO-d6, δ ppm): δ 44.3, 101.4, 139.2, 140.5, 171.2.

Synthesis of M-C-3. The activated ester 9 was synthesized from 8 (1.0 equiv.) by coupling with N-hydroxysuccinimide (HSU, 2.2 equiv.) and N-ethyl-N'-(3-dimethylaminopropyl) carbodiimide hydrochloride (EDC, 2.2 equiv.) in dichloromethane at r.t. for 24 hours. After the removal of the solvent, the crude residue was recrystallized from ethanol to give pure activated ester 9 which was subsequently treated with amine 6 in the presence of trimethylamine in dimethyl sulfoxide (DMSO) at r.t. for 48 hours. Water was then added and the mixture was extracted with dichloromethane (DCM) (50 mL, 3 times). The combined organic layers were washed with brine, dried over anhydrous $Na_2SO_4$ and concentrated to get a pale-yellow crude product which was purified on silica column (ethyl acetate/Hexanes: 0:1 to 1:2) to obtain pure monomer M-C-3 as a white solid (yield, 50%). $^1H$ NMR (300 MHz, DMSO-d6): δ 7.77 (s, 2H), 5.44 (s, 2H), 4.75 (br, s, 6H), 3.55 (s, 4H), 3.05 (m, 12H), 1.64 (m, 12H), 1.43 (s, 54H), 1.35 (m; 12H). $^{13}C$ NMR (75 MHz, DMSO-d6, δ ppm): δ 24.3, 28.6, 32.5, 40.9, 48.3, 59.0, 79.4, 101.1, 139.9, 140.9, 156.3, 168.3. HRMS:(ESI) m/z calcd for $C_{60}H_{104}I_2N_8O_{14}$ [(M+NH4)]+ 1432.6100, found 1432.6097.

Scheme for synthesis of M-C-3

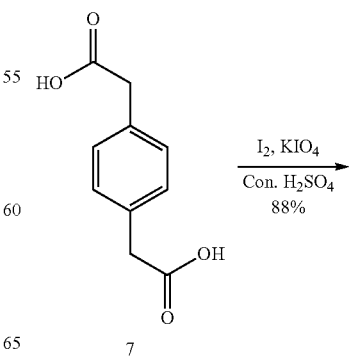

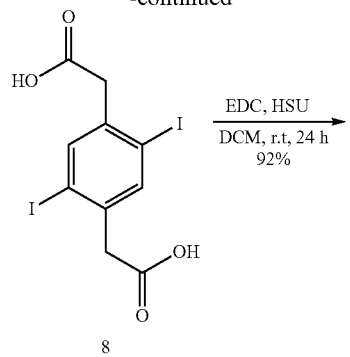

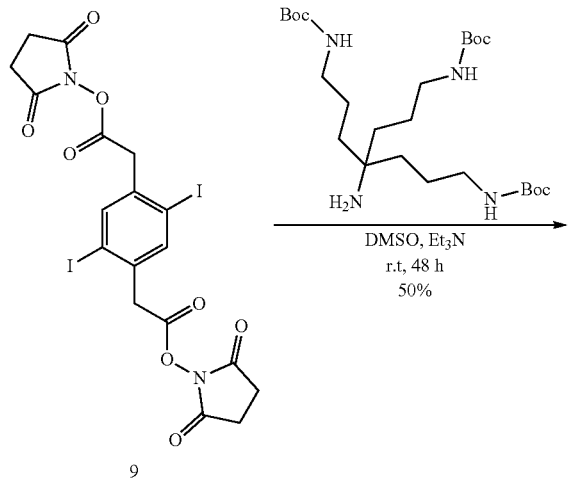

General procedure for synthesis of water soluble CPEs (P-O-3 and P-C-3). Monomer M-O-3 or M-C-3 (100 mg, 1.0 equiv.) and 1,4-diethynylbenzene (1.0 equiv.) were dissolved in 25 mL of THF/Et$_3$N (v/v, 4/1). The resulting solution was deoxygenated with argon for 1 hour. Then 15 mg of Pd(PPh$_3$)$_4$ and 6 mg of CuI were added to the stirred solution under argon. The reaction mixture was then heated up to 55-60° C. and stirred for 48 hours. The viscous solution was then poured into 200 mL of hexane. The precipitate thus formed was collected by vacuum filtration and washed with hexane (200 mL). After drying under vacuum, the polymer was obtained as an amorphous solid. Typical yields for the polymerization reaction are 80-90%. For the hydrolysis of amine protecting group, the organic polymer was dissolved in 20 mL of dioxane and cooled to 0-5 1 C using an ice/water bath. Then concentrated HCl (7 mL, 12 N) was added to the stirring solution dropwise. The reaction mixture was allowed to warm to room temperature and stirred for another 12 hours. The polymer was then precipitated by pouring the solution into a large amount of acetone (200 mL). The precipitate was collected, washed with acetone (100 mL) and then purified by dialysis using 12 kDa molecular weight cutoff (MWCO) dialysis membranes. The water-soluble PPE-CPEs were obtained as yellow solids after freeze drying. P-O-3: $^1$H NMR (300 MHz, DMSO-d6): δ 7.78 (br, s, 4H), 7.38 (s, 2H), 4.94 (s, 4H), 2.97 (br, m, 12H), 1.80 (br, m; 14H), 1.63 (br, m; 12H). P-C-3: $^1$H NMR (300 MHz, DMSO-d6): δ 7.80 (br, s, 4H), 7.62 (s, 2H), 3.04 (s, 4H), 2.90 (s, 12H), 1.65 (br, m; 24H).

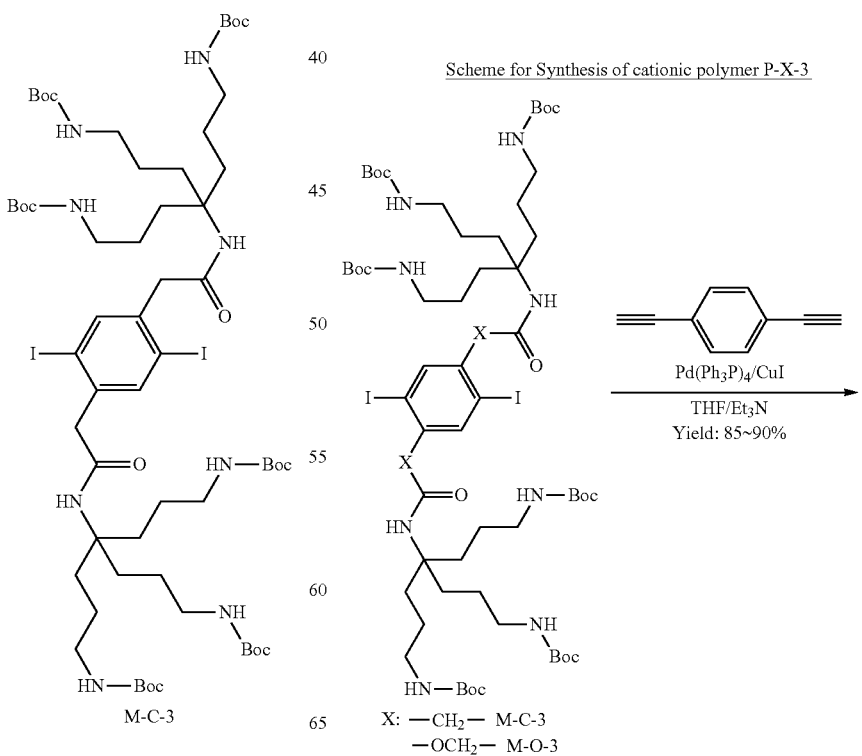

-continued

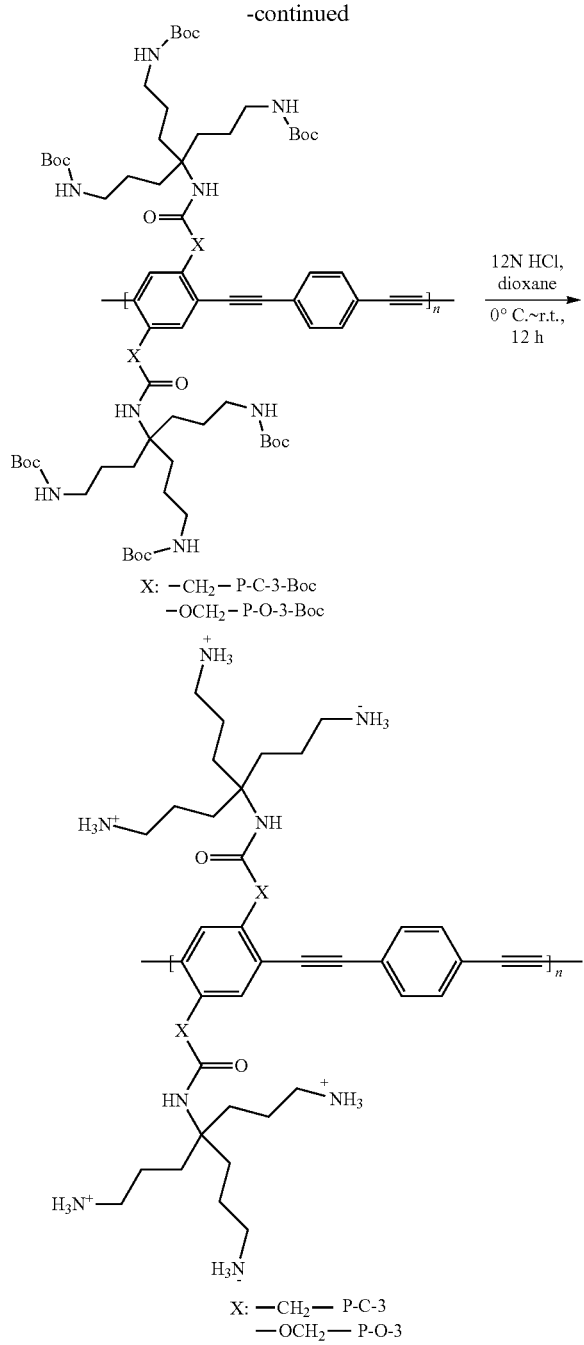

B. CHARACTERIZATION AND USE OF POLYMERIC MARKERS

Classification accuracy. The classification accuracy of a test set with 3 selected wavelengths is 100% using LDA. Accuracy=91.67% for SVM and accuracy=97.22% for KNN.

Figure 3:
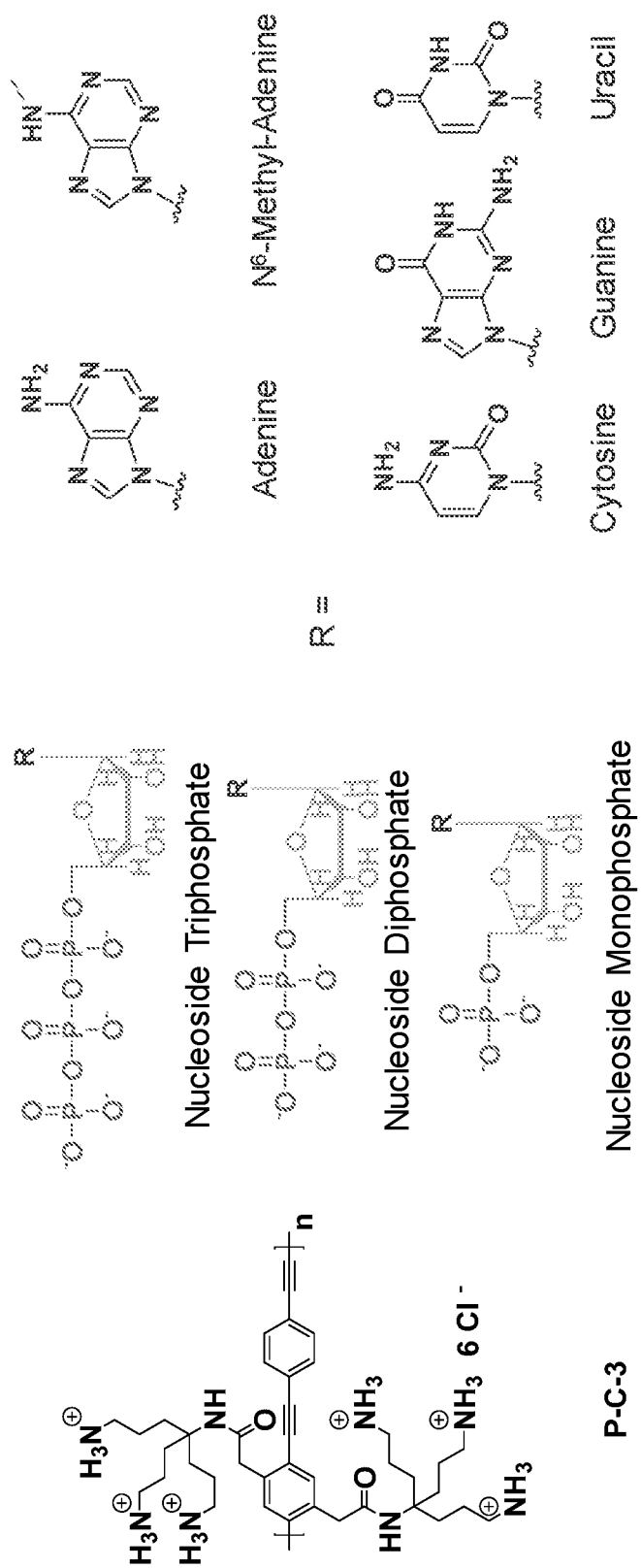
FIG. 3. Structures of P-C-3 and nucleotides with mono-, di-, or tri-phosphates and five nitrogenous bases: Adenine (A), Cytosine (C), Guanine (G), Uracil (U), and $N^6$-methyl adenosine-5'-triphosphate ($N^6$-methyl ATP).
Figure 4:
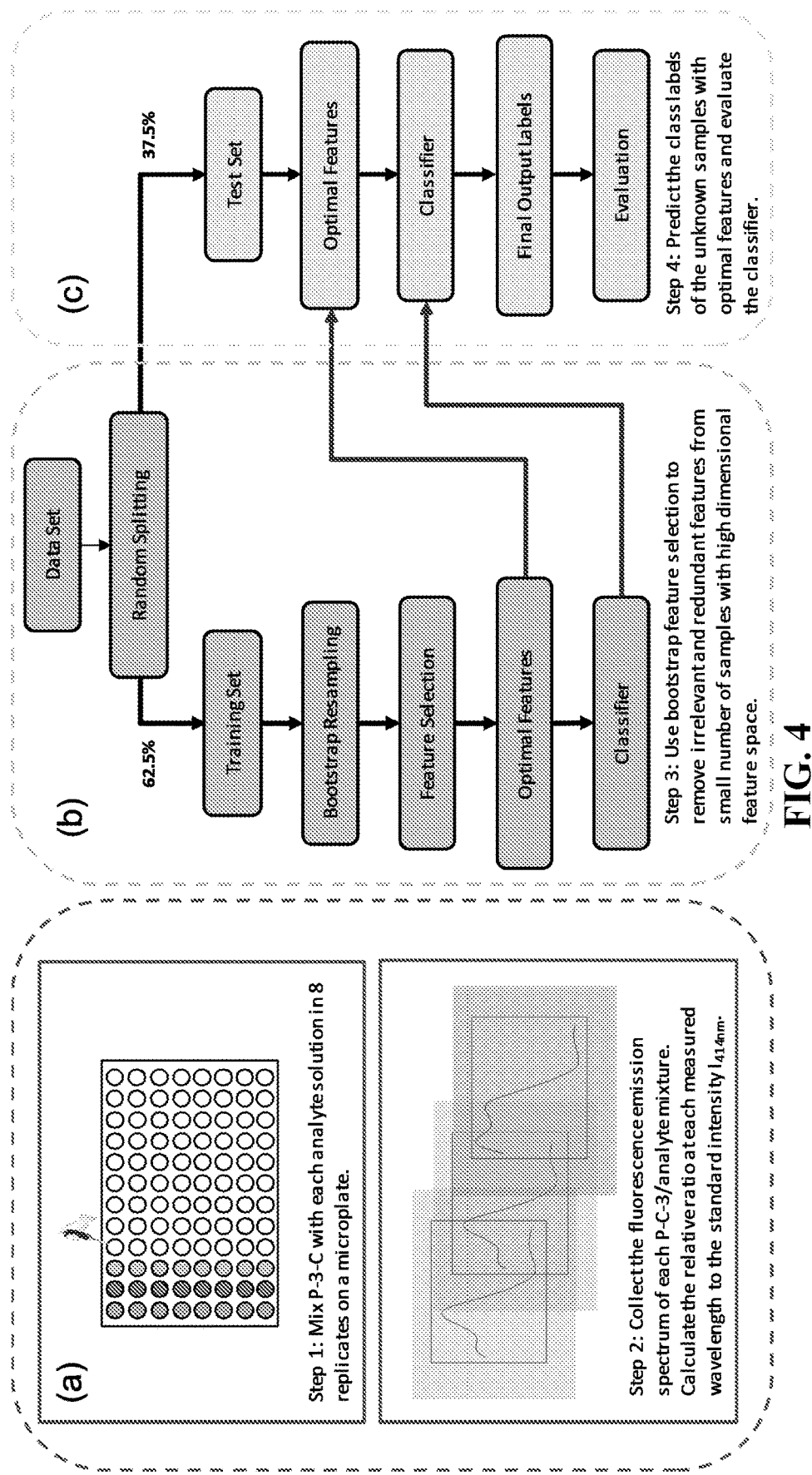
FIG. 4. Schematic illustration of fluorescence spectral shape analysis for nucleotide identification. (a) Illustration of sample preparation and spectral data collection. (b) Flowchart of the feature selection by wrapper approaches and the classifier generation processes. (c) Flowchart of the classifier evaluation and the process of real-world application for unknown sample identification.

The cationic conjugated polyelectrolyte (P-C-3)n (FIG. 3) was evaluated for its ability to serve as a fluorescence sensor for nucleotide recognition. P-C-3 has a fluorescence quantum yield of 27% in water and it provides three —NH3+ units on each side chain which can bind to anionic nucleotides via the phosphate moieties, primarily through electrostatic interactions, as well as other non-specific interactions with nitrogenous bases. (Li et al. (2018) J Mater Chem C 6:3722-30). Nucleotides serve as the biomolecular building blocks of DNA and RNA and are also critical for cellular energetics and signal transduction (Du et al. (2008) Proc Natl Acad Sci USA 105:6409-14). P-C-3 was applied as a broad-spectrum biosensor to classify 13 distinct nucleotides: the mono, di, and tri phosphate forms of adenosine (A), cytosine (C), guanine (G), and uracil (U) as well as methyl-ATP (m⁶A), the most prevalent mammalian messenger RNA (mRNA) modification (Xiang et al. (2017) Nature 543:573; Fu et al. (2014) Nat Rev Genet 15:293).

Figure 5:
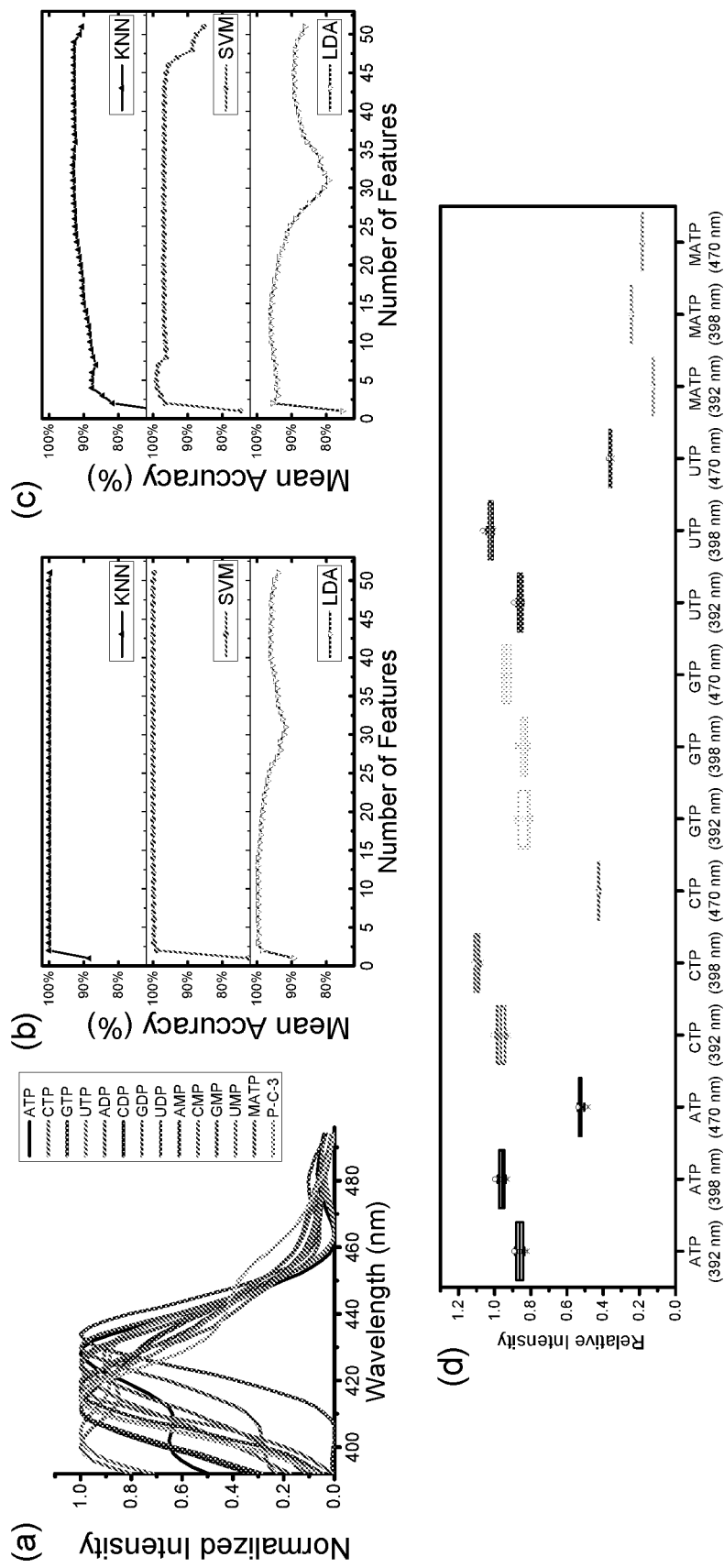
FIG. 5A-5D. (a) Normalized fluorescence emission spectra of all 13 P-C-3/nucleotide mixtures by scaling between 0 and 1. (b) The change of mean classification accuracy against the number of features during sequential floating backward search using LDA, SVM, and k-NN (k=3) classification algorithms. The training set is randomly partitioned from the whole data, and it contains 5 incidences for each P-C-3/nucleotide mixture. The mean classification accuracy is the out-of-bag mean accuracy of 100 bootstrap iterations of the training set. (c) The change of mean classification accuracy against the number of features during sequential floating backward search with the training set plus 10% random error. (d) Boxplot of the 3 optimal features (relative intensities of 392 nm, 398 nm, 470 nm) selected by SVM classification algorithm. The whisker labels represent the standard deviations.

P-C-3 (20 µM) was added to each nucleotide in MES buffer at a consistent 260 nm UV absorption. Normalization to absorption was utilized to allow for the future analysis of unknown or complex mixtures where absorbance, not concentration, could be used as a baseline. Each nucleotide was mixed with P-C-3 in 8 individual microplate wells to generate 104 samples (13 nucleotides×8 replicates). The fluorescence emission spectrum of each P-C-3/nucleotide mixture was collected in 2 nm increments over a range of 392-494 nm at an excitation at 350 nm. The raw spectral data of each instance $I_n$ has p dimensions:

$$I_n = (I_{n392\,nm}, I_{n394\,nm}, I_{n396\,nm}, \ldots, I_{n494\,nm}) \quad (1)$$

where p=52. Unity-based normalization was performed for the fluorescence emission spectrum of each sample to remove the variable of intensity leaving only spectral shape information. In FIG. 5a, it is notable that the normalized emission spectrum of each P-C-3/nucleotide combination has a distinct pattern of emission shape. However, collecting and analyzing the entire fluorescence emission spectrum is not optimal for high-throughput applications. Measuring the fluorescence intensity of every even wavelength from 392 nm to 494 nm generates 52 features, taking approximately 52 times longer than measuring the intensity at a single wavelength. Besides longer data acquisition time, high dimensional spectral data contains a high level of irrelevant and redundant features, which tend to decrease the performance of classification algorithms due to dimensionality (Tang and Liu (2014) Feature Selection for Classification: A Review. Data Classification: Algorithms and Applications (CRC Press, FL)), especially with a small training set.

Feature selection was therefore applied to reduce the dimensionality of the original spectral data. For feature selection and model validation, the data set was randomly partitioned into a training set (65/104) and test set (39/104) with the same instances under each category membership. For real-world applications, instead of using normalized fluorescence intensity, the relative fluorescence intensity @414 nm of each instance is calculated as $$I_{n\,relative} = I_n / I_{n414\,nm} \quad (2)$$

$I_{(n414\,nm\,relative)}$ is always 1, so this element was removed, and the remaining vector was used for the analysis below. The whole feature set contains 51 features that express the relative fluorescence intensity of every even wavelength from 392 nm to 494 nm (except 414 nm) for each instance. These features are highly correlated, so using filter models for feature selection will result in a subset with features concentrated in one region of the spectra. Instead, wrapper models provide a simple way to select a feature subset considering the interaction of the algorithm and the training set (Kohavi and John (1997) Artif Intell 97:273-324; Inza et al. (2004) Artif Intell Med 31:91-103). Since the training set is small compared with the number of features, stratified bootstrap sampling was applied for adding randomness to improve the generalizability for selected features.

To evaluate the feature selection process, three widely used algorithms: linear discriminant analysis (LDA), support vector machines (SVM), and k-nearest neighbors (kNN) were applied and the results were evaluated by classification accuracy. FIG. 5b illustrates the change of mean classification accuracy during the sequential floating backward search. With the full feature set, the mean classification accuracy of LDA is 94.42%. In the process of feature elimination, the mean classification accuracy decreased and reached the local minimum of 91.80% with 31 features, which indicates some irrelevant or redundant features degraded the classifier in accuracy. Then, the mean classification accuracy started to increase and reached 99.74% with only 3 features. For SVM and kNN, the mean classification accuracies are 99.76% and 100% with 3 selected features, and they are both higher than the mean classification accuracies with the full feature set. By adding 10% random error to each feature, FIG. 5c exhibits a more pronounced trend of increasing accuracy with feature elimination and SVM reached 99.08% accuracy with 5 features. The results of sequential floating backward search demonstrate that a small optimal feature set can provide higher average classification accuracy than the original features with lower computational complexity and more generalizability. Since the optimal feature set is small, using forward feature selection from the empty feature set is more efficient. FIG. 5d illustrates the boxplot of the optimal feature set obtained by sequential floating forward search using LDA. Three optimal features are selected, and mean classification accuracies of out-of-bag bootstrap samples were close or equal to 100% for all three classification algorithms when the sequential floating forward search was completed.

TABLE 4

Result of stratified 4-fold repeated cross-validation of LDA, SVM, and k-NN (k = 3) using optimal features for each classification algorithms.

| Classifier | Number of Instances | Number of Features | Number of Folds | Repeated Times | Accuracy (%) |
|---|---|---|---|---|---|
| LDA | 8 | 3 | 4 | 30 | 100% |
| SVM | 8 | 3 | 4 | 30 | 100% |
| KNN | 8 | 3 | 4 | 30 | 100% |

Relative intensities of 398 nm, 464 nm and 468 nm are optimal features for LDA, 392 nm, 398 nm and 470 nm for SVM (linear kernel), and 392 nm, 398 nm and 468 nm for k-NN.

Figure 9:
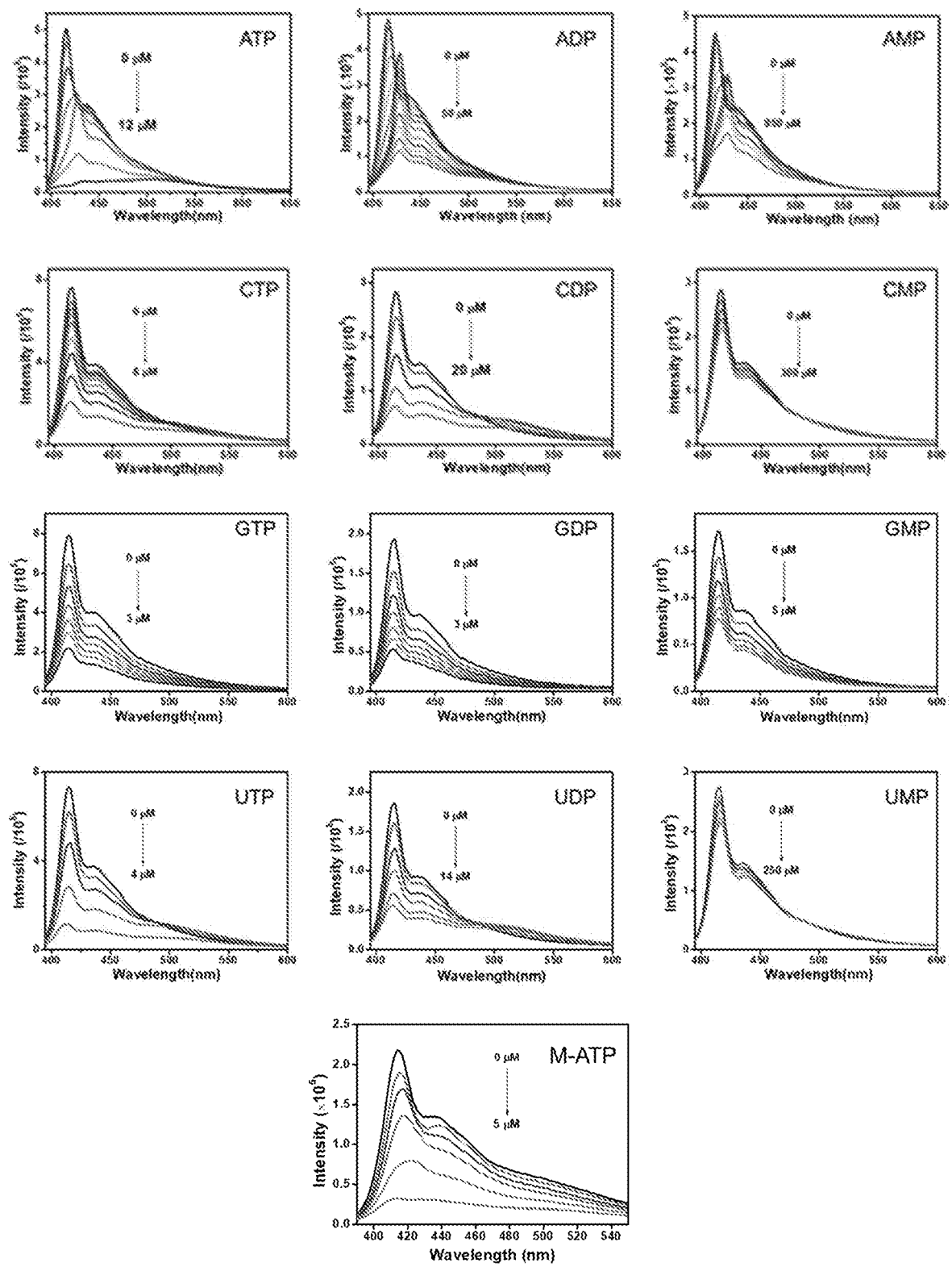
FIG. 9. Fluorescence spectra of P-C-3 in buffered solutions (pH=6.5) with increasing nucleotide concentration. (Polymer concentration=10 µM).

Previous studies have shown that the interaction of P-C-3 with polyphosphate ions in aqueous solution leads to the formation of aggregates (Li et al. (2018) *J Mater Chem C* 6:3722-30). The interchain interactions that occur within these aggregates give rise to the fluorescence quenching and bandshape changes that are the basis of the analysis presented above. The quenching studies are shown in FIG. 9. In order to gain insight into the interactions of P-C-3 with nucleotides and the factors determining the fluorescence emission shape of the conjugated polyelectrolyte, dynamic light scattering (DLS) and atomic force microscopy (AFM) were used to study the size of the P-C-3/nucleotide complexes. The size of all P-C-3/nucleotide complexes were measured by DLS in MES solution with the same concentration used for emission shape analysis. The size of pure P-C-3 was measured by AFM since it is too small to measure by DLS. The mean diameters of all of the P-C-3/nucleotide complexes are larger than that of pure P-C-3 which confirms the formation of aggregates (Table 1). Among these com-

TABLE 1

Size of P-C-3/nucleotide complexes and Stern-Volmer constants of nucleotides. Size of P-C-3/nucleotide complexes are measured by DLS in MES solution. The size of P-C-3 is measured by AFM.

| | P-C-3 | ATP | CTP | GTP | UTP | MATP | ADP | AMP |
|---|---|---|---|---|---|---|---|---|
| Mean Diameter (nm) | 20.2 ± 3.2 | 75.9 ± 0.1 | 394.5 ± 0.1 | 432 ± .01 | 165.9 ± 0.1 | 148.7 ± 0.4 | 57.3 ± 0.1 | 46.2 ± 0.2 |
| $K_{SV}$ ($10^4$ $M^{-1}$) | / | 8.3 | 17.0 | 66.1 | 52.5 | 21.5 | 2.3 | 0.1 |

Size of P-C-3/nucleotide complexes are measured by DLS in MES solution. The size of P-C-3 is measured by AFM. Stern-Volmer constants for nucleotides are measured in 10 μM P-C-3 solution.

Figure 7:
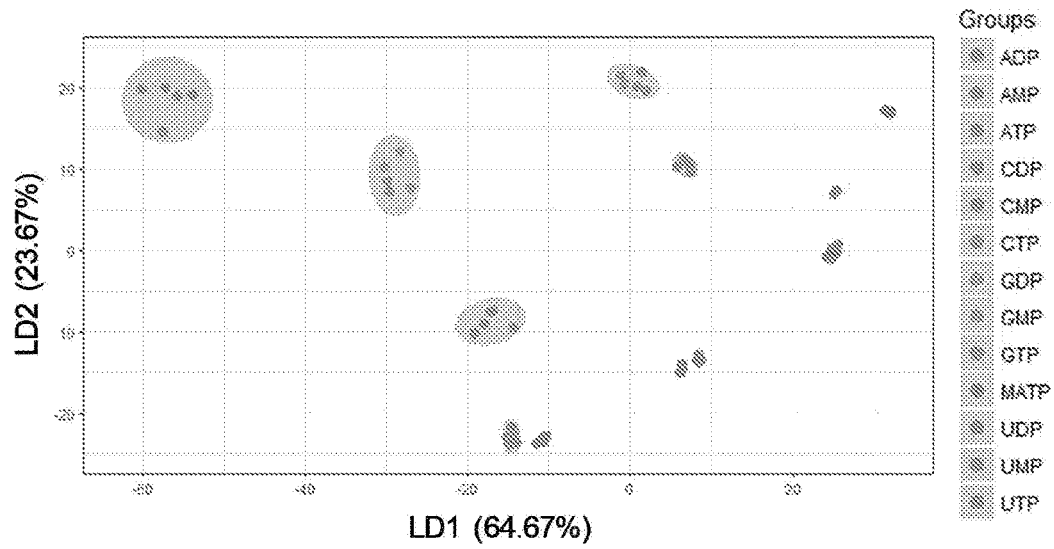
FIG. 7. LDA score plot of 3 selected features for 13 distinct nucleotides. The three features are the relative intensity of 398 nm, 464 nm, and 468 nm. LD1 and LD2 represent 64.67% and 23.69% of total variance. 95% confidence ellipses are shown for each nucleotide.

FIG. 7 demonstrates that the LDA score plot of the 3 selected features with the training set clustered into 13 distinct groups that represent each nucleotide. UMP and CMP clusters appear closest on the plot, but these two groups feature small variances and therefore can still be discriminated with the help of LD3 (11.64% of total variance). The test set split at first was utilized to evaluate the classifier with selected features. Four-fold cross-validation were conducted and repeated 30 rounds with selected features, resulting in a 100% overall classification accuracy for each classification algorithm. Relative intensities of 398 nm, 464 nm, and 468 nm were found to be optimal features for LDA, 392 nm, 398 nm, and 470 nm for SVM (linear kernel), and 392 nm, 398 nm, and 468 nm for kNN with 100% accuracy for each classification algorithm (Table 4). These results demonstrate that the intensities of 3 selected wavelengths plus the intensity of a reference wavelength (414 nm) of P-C-3, were sufficient to classify 13 distinct nucleotides in within 1 minute.

plexes, P-C-3/nucleotide triphosphate complexes are larger than P-C-3/nucleotide di- and monophosphate complexes. This can be explained by the fact that negatively charged phosphate groups of nucleoside triphosphates have stronger electrostatic attractions with the branched amine side groups of P-C-3 than nucleoside diphosphates and monophosphates, leading to larger aggregates. This trend is also supported by Stern-Volmer quenching constants ($K_{sv}$) of nucleotides with P-C-3 (Table 1). The nucleoside triphosphates caused more pronounced aggregation-induced quenching (AIQ) and showed higher $K_{sv}$ values. The nitrogenous base structures also impact aggregate size and fluorescence quenching, indicating that, in addition to electrostatic interactions, hydrophobic interactions and steric interactions between P-C-3 and the nucleotides also influence the self-assembled structures of P-C-3/nucleotide complexes. Interestingly, the $N^6$ methyl derivative of ATP has a Stern-Volmer constant ($K_{sv}$) more than 2 times that of ATP, illustrating that P-C-3 can produce an amplified signal change in response to a small structural difference in the analyte. A reasonable explanation for the significant increase in Ksv is that the $N^6$ methylation of ATP weakens hydrogen bonding between the amine and water, leading to an increase in its hydrophobicity and thus a stronger aggregation with the hydrophobic backbone of P-C-3.

In addition to the aggregation, the overall fluorescence spectral shape is strongly influenced by the conformation of the polymer chains (Yu et al. (2000) Science 289:1327-30). Femtosecond transient absorption was applied to study the rapid photophysical processes of the system. According to the literature (Sheng et al. (2007) Phys Rev B 75:085206), photoinduced absorption can be utilized to study the exciton dynamics on the polymer chain. Photoinduced absorption (PA) global time resolved spectrum from 825 nm to 1000 nm of P-C-3 and P-C-3/ATP was obtained. The PA in this region is assigned to the PA of the singlet exciton of P-C-3, which is comparable with previous reports (Sheng et al. (2007) Phys Rev B 75:085206) and the absorption maximum is around 850 nm, such that the decay of the PA intensity at 850 nm is fitted using the biexponential decay function to obtain two decay lifetimes:

$$I(t) - I_\infty = A_1 e^{\frac{t}{\tau_1}} + A_2 e^{\frac{t}{\tau_2}} \qquad (3)$$

where $A_i$ represents the weight of each rate constant $\tau_i$ and $I_\infty$ is the PA amplitude at time infinity. A kinetic model is proposed to assign these two lifetimes to different kinetic pathways. In Tables 2 and 3, the decay component ($\tau_2$) of P-C-3 is assigned to the rapid energy transfer from isolated polymer chains which has no interchain π-electron delocalization, to aggregated chains where π-electron density is delocalized by interchain interactions (Hardison et al. (2008) J Phys Chem C 112:16140-47). The assignment well explained the decrease in $\tau_2$ and the increase of the amplitude $A_2$ in Table 2, after the addition of nucleotides which promote the formation of aggregates. The energy transfer process competes with the emission process of 'isolated' chains, which influences both the quantum yield and the fluorescence emission shape of P-C-3/nucleotide complexes. Not only does the energy transfer to the aggregates, but the decay processes of 'isolated' chains also influences the fluorescence emission shape. This kinetic model links the long lifetime component ($\tau_1$) to the fluorescence emission and other decay channels in "isolated" chains. After excitation, energy is transferred from the high energy sites to energy traps before emitting or decaying non-radiatively (Hardison et al. (2008) J Phys Chem C 112:16140-47; Yu et al. (2000) Science 289:1327-30). The variation of the long lifetime component ($\tau_1$) between different P-C-3/nucleotide complexes implies that the conformations of 'isolated' chains are also affected by interactions with nucleotides, which influence the fluorescence shape together with the formation of aggregates.

The kinetic model also gives an insight to the signature pattern of fluorescence shape independent of analyte concentration. In Table 3, after the concentration of oligonucleotide exceeded 2 times the molar ratio of P-C-3 chains, the amplitudes of both two decay pathways remain stable. This result demonstrates that the interactions between P-C-3 and the analyte are saturated, and addition of more analyte does not induce additional aggregation or affect the conformation of the 'isolated' polymer chains. This explanation is also supported by the maintenance of the particle sizes of P-C-3/nucleotide complexes when adding more oligonucleotide after the saturation point.

Although this model can explain the general trends of the observations, it is still difficult to predict the lifetime of P-C-3/nucleotide complexes and the fluorescence emission spectral shapes by a simple theoretical model. With the help of machine learning methods, these multi-modal changes in P-C-3 florescence can be utilized for single nucleotide and oligonucleotide classification, which reveals the advantage of using machine learning in the analysis of this complicated system as a complementary methodology in evaluating non-specific interactions in broad-spectrum biosensor design and analysis.

TABLE 2

Photoinduced absorption decay lifetime of P-C-3/nucleotide complexes @ 850 nm when excited by 390 nm pulse.

|       | $A_1$ | $\tau_1$ (ps) | $A_2$ | $\tau_2$ (ps) |
|-------|-------|---------------|-------|---------------|
| P-C-3 | 0.62  | 320 ± 15      | 0.38  | 8.7 ± 0.8     |
| ATP   | 0.49  | 360 ± 12      | 0.51  | 6.7 ± 0.3     |
| CTP   | 0.60  | 368 ± 6       | 0.40  | 7.2 ± 0.3     |
| GTP   | 0.40  | 252 ± 9       | 0.60  | 7.2 ± 0.3     |
| UTP   | 0.40  | 245 ± 18      | 0.60  | 4.4 ± 0.4     |
| MATP  | 0.28  | 139 ± 20      | 0.72  | 2.4 ± 0.4     |
| ADP   | 0.59  | 363 ± 6       | 0.41  | 6.6 ± 0.2     |
| AMP   | 0.58  | 329 ± 6       | 0.42  | 7.9 ± 0.3     |

TABLE 3

Photoinduced absorption decay lifetime of P-C-3 with oligonucleotide sequences @ 850 nm when excited by 390 nm pulse.

| MolarRatio | $A_1$ | $\tau_1$ (ps) | $A_2$ | $\tau_2$ (ps) |
|------------|-------|---------------|-------|---------------|
| 1:1        | 0.38  | 142 ± 8       | 0.62  | 3.9 ± 0.1     |
| 2:1        | 0.20  | 57 ± 5        | 0.80  | 3.8 ± 0.2     |
| 4:1        | 0.24  | 68 ± 9        | 0.76  | 3.8 ± 0.2     |

Traces were fit from the intensity maximum by exponential decay with two lifetimes, and the sum of $A_1$ and $A_2$ are normalized to 1 to reflect their amplitudes.

C. TARGET ANALYTES

In certain aspects a target analyte can be a nucleic acid. The term "target nucleic acid" shall mean a nucleic acid molecule (DNA, RNA, or PNA) whose presence in a sample is to be determined by the probes, methods, and apparatuses of the invention. In general, the terms "target nucleic acid", "nucleic acid molecule,", "nucleic acid sequence," "nucleic acid", "nucleic acid fragment," "oligonucleotide" and "polynucleotide" are used interchangeably and are intended to include, but not limited to, a polymeric form of nucleotides that may have various lengths, either deoxyribonucleotides or ribonucleotides, or analogs thereof. Non-limiting examples of nucleic acids include a gene, a gene fragment, an exon, an intron, intergenic DNA (including, without limitation, heterochromatic DNA), messenger RNA (mRNA), transfer RNA, ribosomal RNA, ribozymes, small interfering RNA (siRNA), non-coding RNA (ncRNA), cDNA, recombinant polynucleotides, branched polynucleotides, plasmids, vectors, isolated DNA of a sequence, isolated RNA of a sequence, nucleic acid probes, and primers.

The present methods can identify a nucleic acid molecule obtained from a sample, e.g., a sample from an organism, and, preferably, without a conversion (or amplification) step.

As an example, for RNA-identifying methods, the present methods do not require conversion of an RNA molecule to a DNA molecule (i.e., via synthesis of cDNA) before the RNA can be identified.

The target nucleic acid can be obtained from any sample or source of nucleic acid, e.g., any cell, tissue, or organism, in vitro, chemical synthesizer, and so forth. The target nucleic acid can be obtained by any art-recognized method. In embodiments, the nucleic acid is obtained from a blood sample of a clinical subject. The nucleic acid can be extracted, isolated, or purified from the source or samples using methods and kits well known in the art.

As will be appreciated by those in the art, the sample may comprise any number of things, including, but not limited to: cells (including both primary cells and cultured cell lines), cell lysates or extracts (including but not limited to RNA extracts; purified mRNA), tissues and tissue extracts (including but not limited to RNA extracts; purified mRNA); bodily fluids (including, but not limited to, blood, urine, serum, lymph, bile, cerebrospinal fluid, interstitial fluid, aqueous or vitreous humor, colostrum, sputum, amniotic fluid, saliva, anal and vaginal secretions, perspiration and semen, a transudate, an exudate (e.g., fluid obtained from an abscess or any other site of infection or inflammation) or fluid obtained from a joint (e.g., a normal joint or a joint affected by disease such as rheumatoid arthritis, osteoarthritis, gout or septic arthritis) of virtually any organism, with mammalian samples being preferred and human samples being particularly preferred; environmental samples (including, but not limited to, air, agricultural, water and soil samples); biological warfare agent samples; research samples including extracellular fluids, extracellular supernatants from cell cultures, inclusion bodies in bacteria, cellular compartments, cellular periplasm, mitochondria compartment.

The biomolecular samples can be indirectly derived from biological specimens. For example, where the target molecule of interest is a cellular transcript, e.g., a messenger RNA, the biomolecular sample of the invention can be a sample containing cDNA produced by a reverse transcription of messenger RNA. In another example, the biomolecular sample of the invention is generated by subjecting a biological specimen to fractionation, e.g., size fractionation or membrane fractionation.

The biomolecular samples of the invention may be either "native," i.e., not subject to manipulation or treatment, or "treated," which can include any number of treatments, including exposure to candidate agents including drugs, genetic engineering (e.g. the addition or deletion of a gene).

A nucleic acid molecule comprising the target nucleic acid may be fragmented by any means known in the art. Preferably, the fragmenting is performed by an enzymatic or a mechanical means. The mechanical means may be sonication or physical shearing. The enzymatic means may be performed by digestion with nucleases (e.g., Deoxyribonuclease I (DNase I)) or one or more restriction endonucleases.

The target nucleic acid can include natural or non-natural nucleotides, comprising modified nucleotides, as well-known in the art.

D. EXAMPLES

The following examples as well as the figures are included to demonstrate preferred embodiments of the invention. It should be appreciated by those of skill in the art that the techniques disclosed in the examples or figures represent techniques discovered by the inventors to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Experiment design. First, dissolve 13 nucleoside phosphates (NTP, NDP, and NMP; N=A, C, G, and U, and methyl-ATP) solution in water, and, the concentration is controlled by having the same UV absorption. Then, add 100 μL equivalent P-C-3 and NXP into a well of a 96-well plate. Measure the emission spectra (from 390 nm to 500 nm) using the plate reader for each well. Repeat that 8 times for each NXP on 96-well plates (8 replicates).

Data analysis. Using the intensity of each even wavelength divided by the intensity @415 nm.

$I390$ nm/$I415$ nm, $I390$ nm/$I415$ nm, $I390$ nm/$I415$ nm . . . , $I498$ nm/$I415$ nm.

The "normalized" intensity from 390 to 498 nm are the new features (55 features in total). The reason to divided the intensity of each wavelength by I415 nm instead of the max intensity is that in the next part, the inventors would like to just measure the intensity of a few wavelengths instead of the whole spectrum, so that the inventors need not find the maximum intensity. Divide 5 of the 8 replicates to the training set to train the algorithm and 3 of the 8 replicates to the test set to measure the accuracy.

All codes are written in R programing language (open source) with MLR and other basic packages. Use the training set for feature selection. Use bootstrapping method (50 iterations) to increase the sample size from 5×13=65 to 5×13×50=3250 to select the more generalized features. Use sequential floating backward search wrapped with linear discriminant analysis (LDA), SVM, and KNN algorithms individually to prove only a few features can achieve the classification of 13 nucleoside phosphates with a high accuracy.

Use sequential floating forward search wrapped with LDA to select features from all 55 features. For LDA, 3 features (390 nm, 402 nm, and 466 nm) are selected. Use the training set to train the LDA algorithm with the only 3 features and then predict the category membership of the test set. The accuracy is 100%.

Now, one only needs to measure, for example, the intensity of 390 nm, 402 nm, 466 nm, and 415 nm (for normalization) instead of the whole spectrum to classify these nucleoside phosphates, which drastically decrease the measuring time and computational complexity.

The same thing is also done for SVM and KNN. The accuracy for SVM is 91.67% and for KNN is 97.22%. The accuracy can be increased by tuning some parameters, but it is not necessary since LDA performs well.

Example 2

Figure 8:
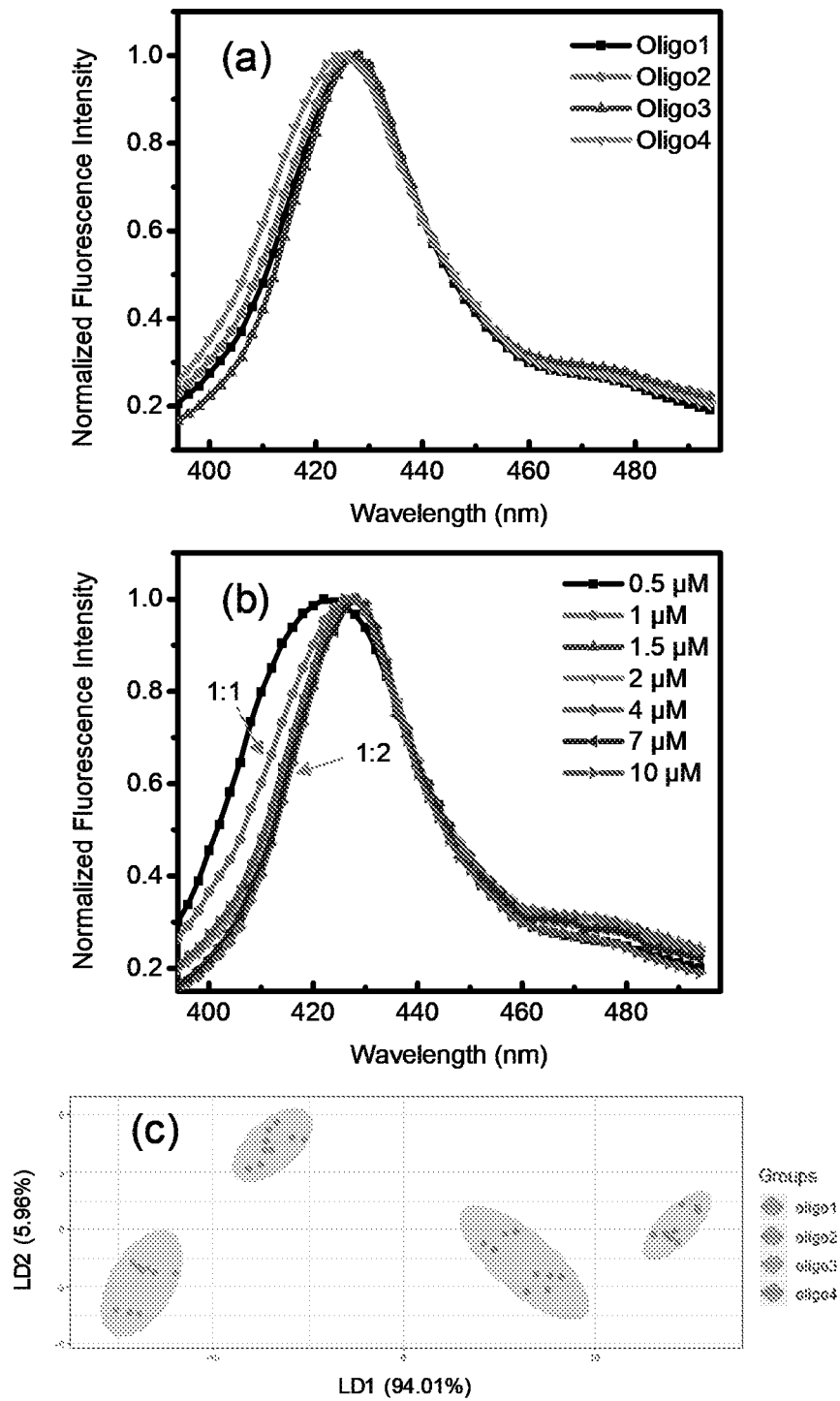
FIG. 8a-8c. (a) Normalized fluorescence emission spectra of all P-C-3/oligonucleotide mixtures at 10 µM (~1 µM in polymer chains). (b) Normalized fluorescence emission spectra of P-C-3/Oligo3 at 0.5-10 µM. The lines of representing a ratio of P-C-3:oligonucleotide of 1:1 and 1:2 are marked by arrows. (c) LDA score plot of 3 selected features for 4 oligonucleotides. The three features are relative intensity of 402 nm, 434 nm, and 492 nm. LD1 and LD2 represent 94.01% and 5.69% of total variance. 95% confidence ellipses are shown for each oligonucleotide.

The sensitivity and stability of fluorescence spectral shape analyses were further analyzed using DNA oligonucleotides. Four oligonucleotide sequences were evaluated: two sequences of 21 bases (oligo1 and oligo2) and two sequences of 34 bases (oligo3 and oligo4), with each size-matched pair containing an equivalent purine to pyrimidine ratio, but with different individual nucleotides (Table 5). Oligonucleotides (Sigma Aldrich) were dissolved in DNAse, RNAse free, UltraPure™ Distilled Water (Invitrogen) to create a stock concentration of 100 µM. Each oligonucleotide was mixed with 10 µM P-C-3 (~1 µM in polymer chains) in MES buffer and the fluorescence spectra were collected as described above for single nucleotides. FIG. 8a shows these four oligonucleotides have distinct fluorescence spectral shapes when mixed with P-C-3. As demonstrated for oligo3 in FIG. 8b, the saturation was detected at a 1:2 molar ratio between P-C-3 chains and oligonucleotide, which indicates stability of the fluorescence spectral shape is not affected by the variation of concentration as long as the oligonucleotide is 2 times more concentrated than P-C-3. To further illustrate this point, four replicates of each oligonucleotide at 4, 7, and 10 µM were used in the data set and assigned to the same membership, resulting in 12 instances for each oligonucleotide. Three features, the relative intensities of 402, 434 and 492 nm, were selected by LDA using the feature selection method described above. FIG. 8c shows the LDA score plot and the 50 times repeated six-fold cross-validation gave a 100% accuracy (Table 6). This perfect accuracy demonstrates that the fluorescence spectral shape analysis is sensitive to differences in complicated macromolecular analytes represented by distinct oligonucleotide sequences. The discovery of the saturation point enables spectral shape analysis using the signature pattern associated with the structure independent of analyte concentration, which constitutes a major advantage over intensity-based sensors.

TABLE 5

DNA oligonucleotide information.

| | Molecular Weight (g/mol) | Number of Bases | Purine Content (%) | Sequence (5'-3') |
|---|---|---|---|---|
| oligo1 | 6483 | 21 | 47.6 | CTGTGGATTGGAGC GATTCTT (SEQ ID NO: 1) |
| oligo2 | 6399 | 21 | 47.6 | TTACAACGGCTGAT AGCACCA (SEQ ID NO: 2) |
| oligo3 | 10626 | 34 | 58.8 | GTAGGTTGGTGTGG TCGCCTTCAGAGTG CGGAAG (SEQ ID NO: 3) |
| oligo4 | 10262 | 34 | 58.8 | CTTCCGCACTCTGA AGGCGACCACACCA ACCTAC (SEQ ID NO: 4) |

TABLE 6(a)

Data set for oligonucleotide classification

| Oligo-nucleotide | 4 uM | 7 uM | 10 uM | Total Instances |
|---|---|---|---|---|
| Oligo1 | 4 | 4 | 4 | 12 |
| Oligo2 | 4 | 4 | 4 | 12 |
| Oligo3 | 4 | 4 | 4 | 12 |
| Oligo4 | 4 | 4 | 4 | 12 |

TABLE 6(b)

Result of stratified 6-fold repeated cross-validation of LDA, SVM, and k-NN (k = 3) classification algorithms using the optimal features for each classification algorithm.

| Classifier | Number of Instances | Number of Features | Number of Folds | Repeated Times | Accuracy (%) |
|---|---|---|---|---|---|
| LDA | 12 | 3 | 4 | 50 | 100% |
| SVM | 12 | 3 | 4 | 50 | 100% |
| KNN | 12 | 3 | 4 | 50 | 100% |

Relative intensities of 398 nm, 464 nm and 468 nm are optimal features for LDA, 392 nm, 398 nm and 470 nm for SVM (linear kernel), and 392 nm, 398 nm and 468 nm for k-NN.
Reference intensity: 414 nm.

Materials—All nucleotides were purchased from Sigma-Aldrich and stock solutions were prepared in water with the same absorption at 260 nm as 20 µL ATP. $N^6$-Methyl-ATP was purchased from TriLink Biotechnologies and a stock solution was prepared in the same manner. A stock solution of 2-(N-morpholino)ethanesulfonic acid (MES) buffer solution (pH 6.5) was prepared at 10 mM. The synthesis and characterization of P-C-3 are described in Li et al. (2018) *J Mater Chem C* 6:3722-30. The number-average molecular weights (Mn) for the P-C-3-Boc is 12 kDa with PDI=2.2. Oligonucleotides were purchased from Sigma-Aldrich and dissolved in DNAse, RNAse free, UltraPure™ Distilled Water (Invitrogen) to create a stock concentration of 100 µM.

Fluorescence Quenching—Steady-state fluorescence spectra were recorded with a PTI Quanta Master spectrometer (Photon Technology International). In quenching experiments, 2 mL of 10 µM P-C-3 solution was added to a 1 cm square quartz fluorescence cuvette. Then fluorescence spectra were collected after adding microliter aliquots of a concentrated nucleotide solutions. The quenching experiment was terminated when approximately 90% of the fluorescence was observed to be quenched or no more fluorescence can be quenched. The linear section of the plot was fitted according to the Stern-Volmer (SV) equation $I_0/I = 1 + K_{sv}[Q]$. FIG. 9 shows the P-C-3 fluorescence spectra as a function of added quencher concentration for each nucleoside.

Figure 6:
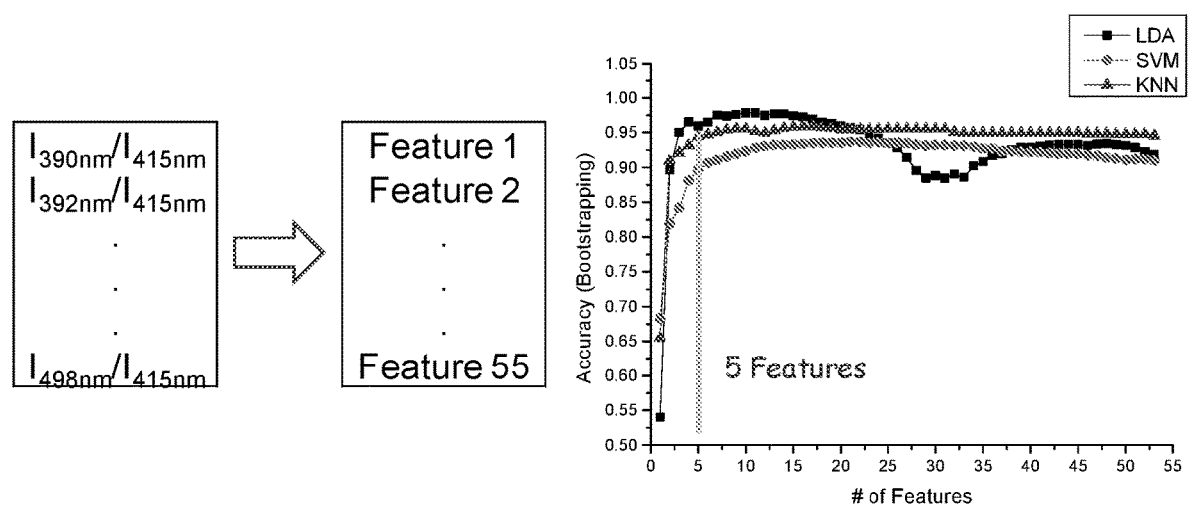
FIG. 6. Features selection. The sample size is increased to 3000 by bootstrapping to select the most generalized features. A new predictive model with selected features is created with a high accuracy while requiring less than 5 features.
Figure 10:
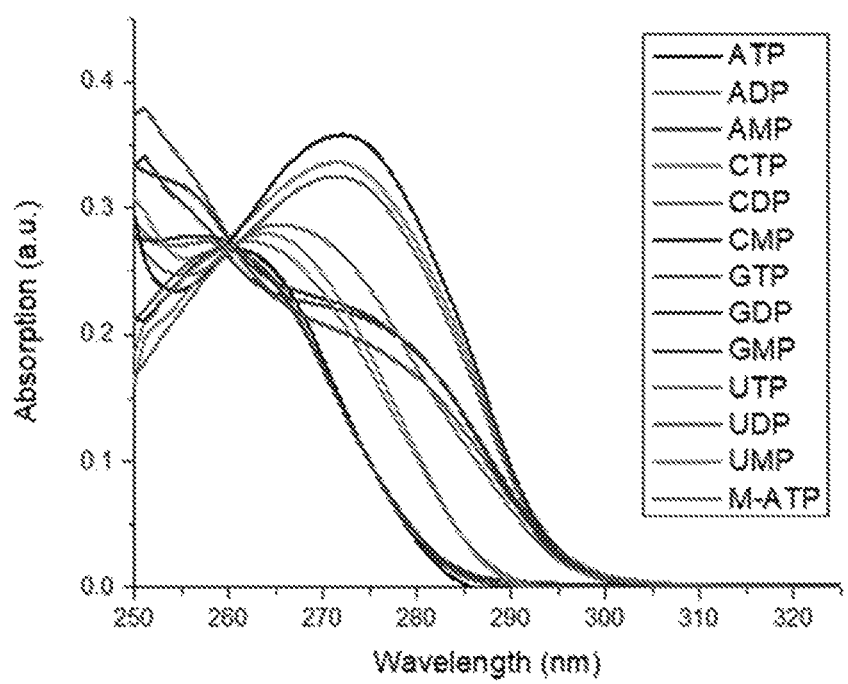
FIG. 10. Absorption of 13 nucleotides in water.

Classification Method—All emission spectra were obtained by BioTek Synergy H1 Hybrid Multi-Mode Reader using monochromators. UV-visible spectra were obtained by a Varian Cary 100 dual-beam spectrophotometer. All codes were written in R programing language (open source) with MLR package and other basic packages. Method development flow is illustrated in FIG. 6. In the first step, 100 µL of P-C-3 solution (20 µM in MES) was added with each nucleotide equivalently at a consistent 260 nm UV absorption (FIG. 10). Normalization to absorption was utilized to allow for the future analysis of unknown or complex mixtures where absorbance, not concentration, could be used as a baseline because it is difficult to measure the concentration of an unknown analyte, but it is easy to measure the absorption. Measure the emission spectra from 392 nm to 494 nm (excited at 350 nm) using the plate reader for each well. Repeat that 8 times for each P-C-3/nucleotide complex on 96-well plates (8 replicates). A repository was created containing the code in R programming language for data analysis. Randomly split 5 of the 8 replicates to the training set to train the algorithm and 3 of the 8 replicates to the test set to measure the accuracy. Use the training set for feature selection. Bootstrapping were used to resample the data (100 iterations) and sequential floating forward search wrapped with LDA, SVM, and kNN (k=3) algorithms was applied to select optimal features. Stratified four-fold cross validation was repeated for 30 times and the result is shown in Table 4. For the classification of oligonucleotides (Table 5), each oligonucleotide at 4, 7, and 10 µM were mixed in the data set resulting 12 instances for each membership (Table 6a). Optimal features were selected using the method described above with 10% random error. 100% accuracy was achieved using optimal features for LDA, SVM, and k-NN (k=3) algorithms (Table 6b).

Dynamic light scattering (DLS)—Dynamic light scattering (DLS) and fluorescence lifetimes are measured using the same methods reported in Huang Y, et al. (2017) *Chem Mater* 29:6389-6395.

Figure 11:
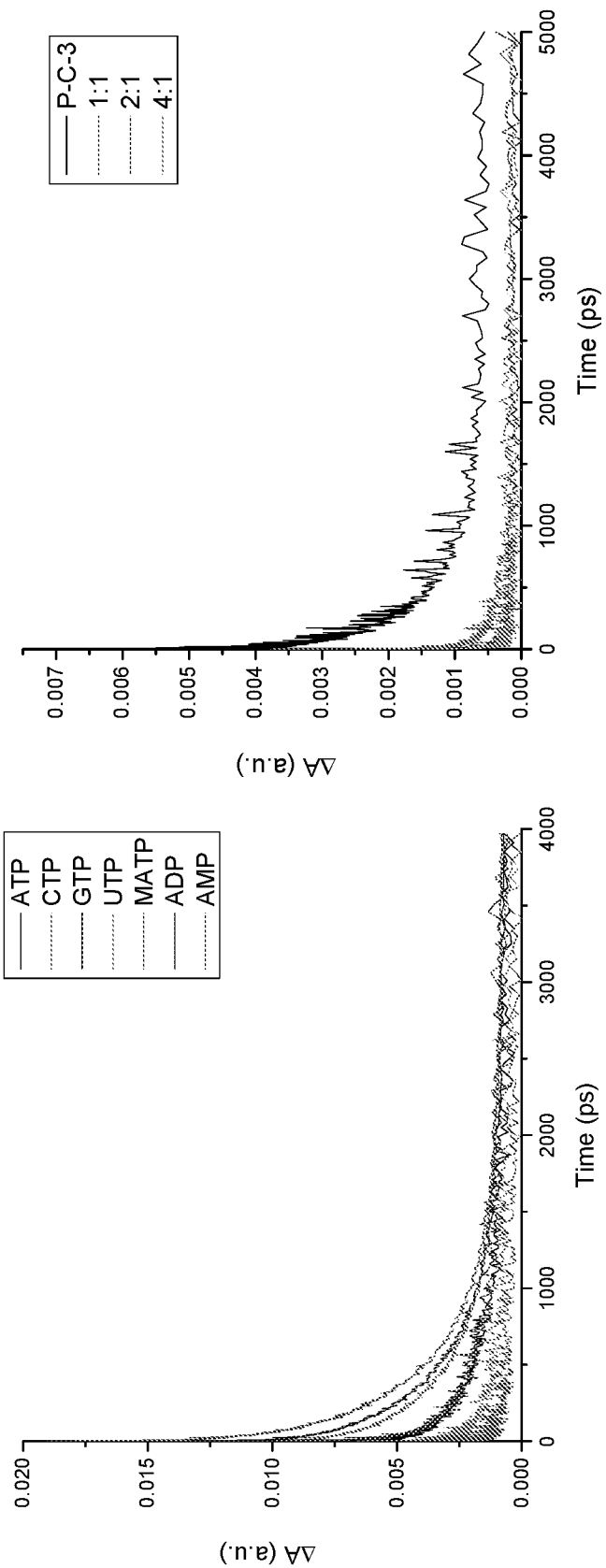
FIG. 11. The change in ΔA with time at 850 nm for all nucleotides and oligonucleotides.

Transient absorption spectroscopy—Subpicosecond transient absorption spectroscopy was performed using the pump-probe technique by taking the fundamental 800 nm laser beam generated by an Astrella Ti:Sapphire Amplifier (120 fs, 1 kHz) and splitting it into two beams. Sufficient power for both beams was dumped so as to not induce damage to any optics. One beam was directed through a Coherent OperA Solo optical parametric amplifier where the excitation wavelength was tuned to 390 nm for pumping. Both beams were then guided into a HELIOS Femtosecond Transient Absorption Spectrometer manufactured by Ultrafast Systems where the 390 nm pump passed through a chopper, reducing its repetition rate by half, and a neutral density filter to adjust average power to 0.1 mW (100 nJ/pulse). The 800 nm beam was passed through a computer-controlled delay stage with a usable range of up to 8 ns followed by an Ultrafast Systems proprietary crystal for NIR continuum (820 nm to 1500 nm) generation for probing. The two beams were overlapped at the sample position with their respective electronic polarizations at the magic angle. Absorption spectra with and without pumping were collected with a 256 pixel InGaAs fiber-coupled spectrometer to produce an array of absorption difference spectra at different time delays. Chirp corrections were employed using software supplied by Ultrafast Systems. The corrected change in $\Delta$O.D. with time at 850 nm was taken from the difference spectra to fit kinetic traces for all nucleotides and oligonucleotide 3 (FIG. 11), and the summary of regression parameters are shown in Table 7. The concentration of P-C-3 was doubled to 20 µM (~2 µM in polymer chains) for transient absorption in order to get enough intensity.

TABLE 7

Summary of regression parameters.

|  | y0 | A1 | t1 | A2 | t2 | Reduced Chi-Sqr | Adj. R-Square |
|---|---|---|---|---|---|---|---|
| P-C-3 | 7.13E−04 | 3.08E−03 | 3.19E+02 | 2.30E−03 | 8.70E+00 | 8.66E−08 | 0.97 |
| 1:1 | 2.31E−04 | 3.06E−03 | 3.87E+00 | 1.02E−03 | 1.42E+02 | 1.45E−08 | 0.98 |
| 2:1 | 1.59E−04 | 2.45E−03 | 3.83E+00 | 6.93E−04 | 5.70E+01 | 8.60E−09 | 0.98 |
| 4:1 | 1.38E−04 | 4.50E−04 | 6.84E+01 | 2.12E−03 | 3.83E+00 | 9.93E−09 | 0.96 |
| ATP | 8.26E−04 | 4.02E−03 | 3.60E+02 | 4.14E−03 | 6.70E+00 | 8.12E−08 | 0.98 |
| CTP | 1.09E−03 | 4.48E−03 | 7.22E+00 | 6.83E−03 | 3.67E+02 | 5.21E−08 | 0.99 |
| GTP | 1.12E−03 | 6.79E−03 | 7.18E+00 | 4.45E−03 | 2.52E+02 | 1.19E−07 | 0.98 |
| UTP | 7.01E−04 | 2.35E−03 | 2.44E+02 | 3.47E−03 | 4.40E+00 | 1.48E−07 | 0.91 |
| MATP | 4.98E−04 | 1.46E−03 | 1.39E+02 | 3.75E−03 | 2.36E+00 | 2.35E−07 | 0.72 |
| ADP | 1.03E−03 | 8.23E−03 | 3.63E+02 | 5.66E−03 | 6.56E+00 | 7.95E−08 | 0.99 |
| AMP | 1.22E−03 | 7.62E−03 | 7.94E+00 | 1.07E−02 | 3.29E+02 | 1.45E−07 | 0.99 |

Figure 12:
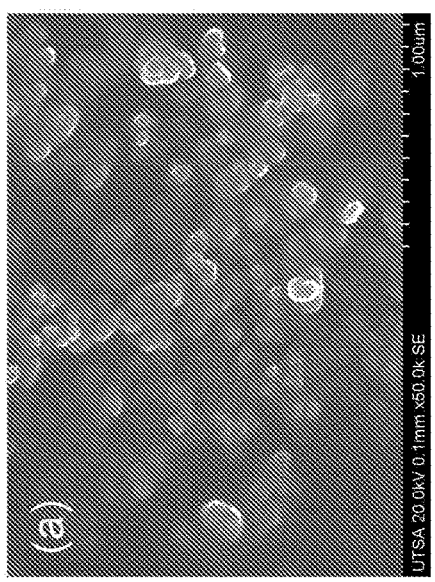
FIG. 12a-12c. SEM images of P-C-3 aggregates with (a) 1, (b) 2, and (c) 5 µM oligonucleotide 3.
Figure 12:
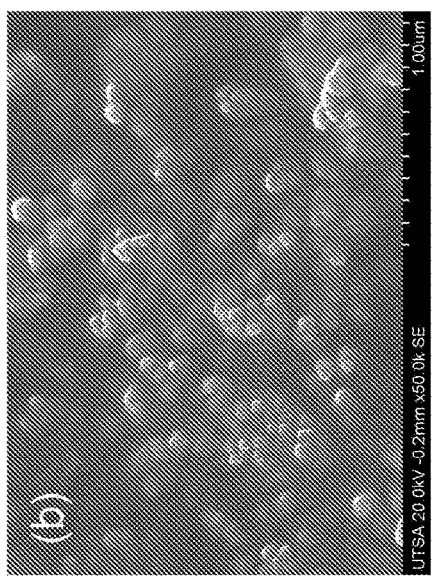
Figure 12:
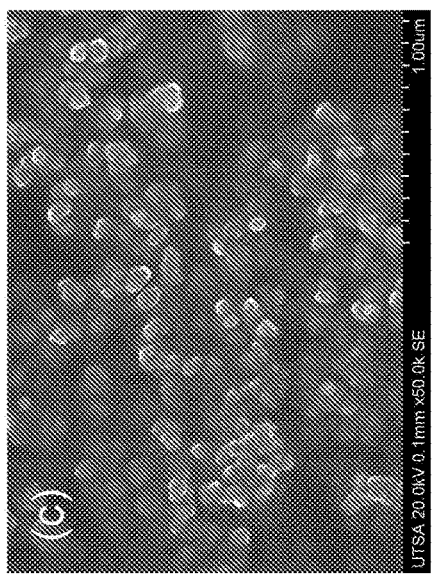

Scanning Electron Microscopy (SEM)—P-C-3 (~1 µM in polymer chains) and oligonucleotide 3 from 1 to 5 µM were mixed in water and freeze-dried as samples. Scanning electron microscopy (SEM) measurement was carried out in Hitachi STEM S5500 at an accelerating voltage of 20 kV. The average and standard deviation were calculated using 50 particles. The size of P-C-3/oligonucleotide 3 aggregates were 58.6±12.5 nm, 73.2±14.4 nm, and 74.6±16.6 nm for 1, 2, and 5 µM oligonucleotide 3, respectively (FIG. 12).

Figure 13:
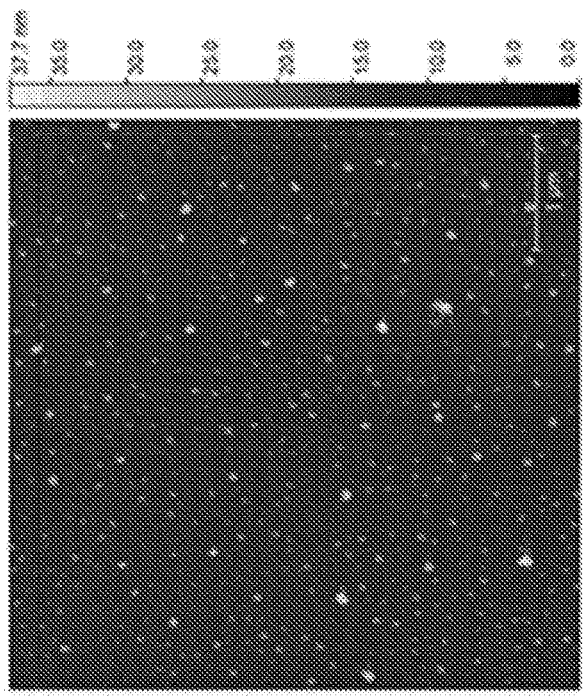
FIG. 13. AFM image of P-C-3 on mica.
Figure 13:
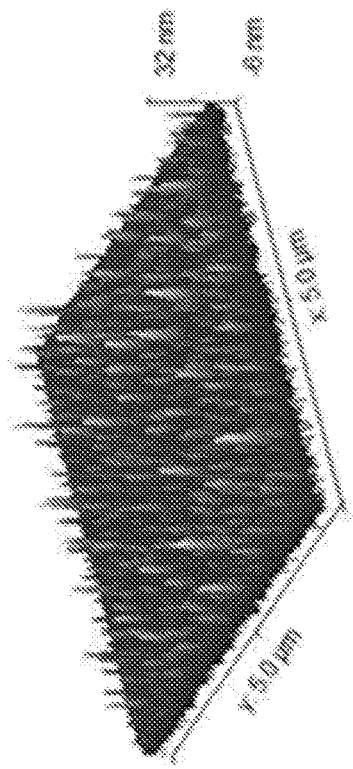

Atomic Force Microscopy (AFM)—AFM was carried out using a Bruker instrument. AFM image of P-C-3 on mica was obtained using tapping mode (FIG. 13).

The invention claimed is:

1. A method of identifying an analyte in a sample comprising:
   contacting the analyte, wherein the analyte is a nucleoside, a nucleotide, a nucleotide diphosphate, or a nucleotide triphosphate, with a polycation polymer forming an analyte/polycation polymer complex, wherein the polycation polymer is a P-C-3 polymer having the chemical structure below

P-C-3

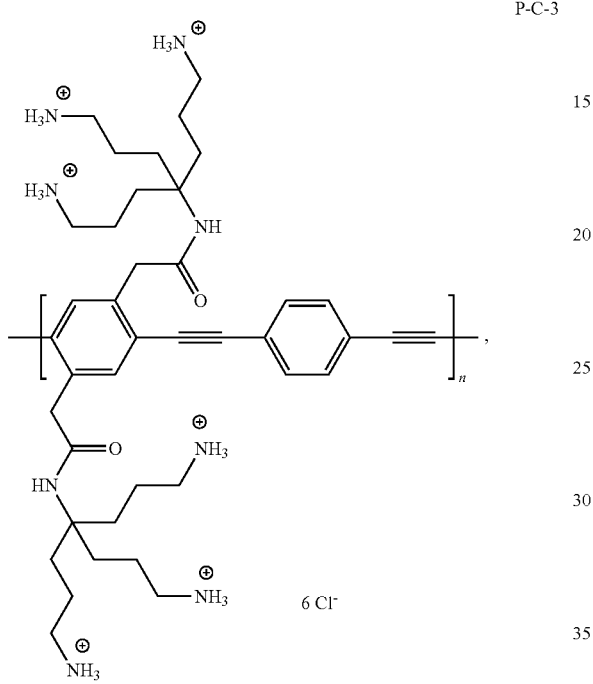

where n is 3 to 1000;
   exposing the analyte/polycation polymer complex to one or more excitation wavelengths of light;
   detecting an emission spectra at two or more selected wavelengths and a reference wavelength; and
   identifying the analyte by analyzing the emission spectra.

2. The method of claim 1, wherein the analyte is a nucleoside phosphate.

3. The method of claim 1, wherein n is 500 to 1000.

4. The method of claim 1, wherein the emission spectra of at least three selected wavelengths are detected.

5. The method of claim 1, wherein the analyte is identified in 30 seconds to 1.5 minute.

* * * * *